(12) United States Patent
Martin et al.

(10) Patent No.: US 9,125,645 B1
(45) Date of Patent: Sep. 8, 2015

(54) RECIPROCATING NEEDLE DRIVE WITHOUT CABLES

(71) Applicant: Ethicon Endo-Surgery, Inc., Cincinnati, OH (US)

(72) Inventors: David T. Martin, Milford, OH (US); Wells D. Haberstich, Loveland, OH (US); James A. Woodard, Jr., Apex, NC (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 67 days.

(21) Appl. No.: 13/792,947

(22) Filed: Mar. 11, 2013

(51) Int. Cl.
*A61B 17/00* (2006.01)
*A61B 17/04* (2006.01)

(52) U.S. Cl.
CPC .................. *A61B 17/0469* (2013.01)

(58) Field of Classification Search
CPC .................. A61B 17/0482; A61B 2017/0498; A61B 17/06
USPC .................. 606/139, 144–149, 232; 227/901
See application file for complete search history.

(56) References Cited

U.S. PATENT DOCUMENTS

| | | |
|---|---|---|
| 1,203,244 A | 10/1916 | Nash |
| 1,579,379 A | 4/1926 | Marbel |
| 1,822,330 A | 9/1931 | Ainslie |
| 2,291,181 A | 7/1942 | Alderman |
| 3,168,097 A | 2/1965 | Dormia |
| 3,749,238 A | 7/1973 | Taylor |
| 4,027,608 A | 6/1977 | Arbuckle |
| 4,203,430 A | 5/1980 | Takahashi |
| 4,557,265 A | 12/1985 | Andersson |
| 4,624,254 A | 11/1986 | McGarry et al. |
| 4,880,015 A | 11/1989 | Nierman |
| 4,899,746 A | 2/1990 | Brunk |
| 4,942,866 A | 7/1990 | Usami |
| 5,020,514 A | 6/1991 | Heckele |
| 5,209,747 A | 5/1993 | Knoepfler |
| 5,282,806 A | 2/1994 | Haber et al. |
| 5,289,963 A | 3/1994 | McGarry et al. |
| 5,306,281 A | 4/1994 | Beurrier |
| 5,308,353 A | 5/1994 | Beurrier |

(Continued)

FOREIGN PATENT DOCUMENTS

| | | |
|---|---|---|
| DE | 4310315 | 10/1993 |
| DE | 4300307 | 7/1994 |

(Continued)

OTHER PUBLICATIONS

U.S. Appl. No. 61/355,832, filed Jun. 17, 2010.

(Continued)

*Primary Examiner* — Katrina Stransky
*Assistant Examiner* — Mikail Mannan
(74) *Attorney, Agent, or Firm* — Frost Brown Todd LLC

(57) ABSTRACT

An apparatus includes a housing, a drive gear assembly, and a drive arm. The housing defines a channel that receives a needle such that the needle is movable within the channel. The drive gear assembly is positioned within the housing and includes a first gear, a second gear, and a rack. The rack is translatable relative to the housing and is coupled with the first and second gears to rotate the first and second gears. The drive arm is coupled with the drive gear assembly and engages the needle to move the needle within the channel of the housing.

20 Claims, 32 Drawing Sheets

(56) References Cited

U.S. PATENT DOCUMENTS

| | | | |
|---|---|---|---|
| 5,318,578 A | 6/1994 | Hasson | |
| 5,330,502 A | 7/1994 | Hassler et al. | |
| 5,383,888 A | 1/1995 | Zvenyatsky et al. | |
| 5,403,347 A | 4/1995 | Roby et al. | |
| 5,403,354 A | 4/1995 | Adams et al. | |
| 5,437,681 A | 8/1995 | Meade et al. | |
| 5,454,823 A | 10/1995 | Richardson et al. | |
| 5,470,338 A * | 11/1995 | Whitfield et al. | 606/144 |
| 5,478,344 A | 12/1995 | Stone et al. | |
| 5,478,345 A | 12/1995 | Stone et al. | |
| 5,480,406 A | 1/1996 | Nolan et al. | |
| 5,527,321 A * | 6/1996 | Hinchliffe | 606/144 |
| 5,540,704 A | 7/1996 | Gordon et al. | |
| 5,540,705 A | 7/1996 | Meade et al. | |
| 5,540,706 A | 7/1996 | Aust et al. | |
| 5,549,542 A | 8/1996 | Kovalcheck | |
| 5,553,477 A | 9/1996 | Eisensmith et al. | |
| 5,554,170 A | 9/1996 | Roby et al. | |
| 5,560,532 A | 10/1996 | DeFonzo et al. | |
| 5,569,301 A | 10/1996 | Granger et al. | |
| 5,571,090 A | 11/1996 | Sherts | |
| 5,591,181 A | 1/1997 | Stone et al. | |
| 5,607,450 A | 3/1997 | Zvenyatsky et al. | |
| 5,610,653 A | 3/1997 | Abecassis | |
| 5,617,952 A | 4/1997 | Kranendonk | |
| 5,630,825 A | 5/1997 | de la Torre et al. | |
| 5,632,432 A | 5/1997 | Schulze et al. | |
| 5,632,746 A * | 5/1997 | Middleman et al. | 606/78 |
| 5,669,490 A | 9/1997 | Colligan et al. | |
| 5,674,229 A | 10/1997 | Tovey et al. | |
| 5,674,230 A | 10/1997 | Tovey et al. | |
| 5,693,071 A | 12/1997 | Gorecki et al. | |
| 5,707,379 A | 1/1998 | Fleenor et al. | |
| 5,709,693 A | 1/1998 | Taylor | |
| 5,713,910 A | 2/1998 | Gordon et al. | |
| 5,728,107 A | 3/1998 | Zlock et al. | |
| 5,728,108 A | 3/1998 | Griffiths et al. | |
| 5,733,293 A | 3/1998 | Scirica et al. | |
| 5,741,277 A | 4/1998 | Gordon et al. | |
| 5,759,188 A | 6/1998 | Yoon | |
| 5,766,186 A | 6/1998 | Faraz et al. | |
| 5,766,196 A | 6/1998 | Griffiths | |
| 5,776,186 A | 7/1998 | Uflacker | |
| 5,792,135 A | 8/1998 | Madhani et al. | |
| 5,792,151 A | 8/1998 | Heck et al. | |
| 5,814,054 A | 9/1998 | Kortenbach et al. | |
| 5,817,084 A | 10/1998 | Jensen | |
| 5,860,992 A | 1/1999 | Daniel et al. | |
| 5,865,836 A | 2/1999 | Miller | |
| 5,871,488 A | 2/1999 | Tovey et al. | |
| 5,878,193 A | 3/1999 | Wang et al. | |
| 5,888,192 A | 3/1999 | Heimberger | |
| 5,897,563 A | 4/1999 | Yoon et al. | |
| 5,904,667 A | 5/1999 | Falwell | |
| 5,908,428 A | 6/1999 | Scirica et al. | |
| 5,911,727 A | 6/1999 | Taylor | |
| 5,921,956 A | 7/1999 | Grinberg et al. | |
| 5,938,668 A | 8/1999 | Scirica et al. | |
| 5,947,982 A | 9/1999 | Duran | |
| 5,954,731 A | 9/1999 | Yoon | |
| 5,954,733 A | 9/1999 | Yoon | |
| 5,976,074 A | 11/1999 | Moriyama | |
| 5,993,381 A | 11/1999 | Ito | |
| 5,993,466 A | 11/1999 | Yoon | |
| 6,016,905 A | 1/2000 | Gemma et al. | |
| 6,056,771 A | 5/2000 | Proto | |
| 6,071,289 A | 6/2000 | Stefanchik et al. | |
| 6,086,601 A | 7/2000 | Yoon | |
| 6,126,666 A | 10/2000 | Trapp et al. | |
| 6,135,385 A | 10/2000 | Martinez de Lahidalga | |
| 6,136,010 A | 10/2000 | Modesitt et al. | |
| 6,138,440 A | 10/2000 | Gemma | |
| 6,162,208 A | 12/2000 | Hipps | |
| 6,231,565 B1 | 5/2001 | Tovey et al. | |
| 6,332,888 B1 | 12/2001 | Levy et al. | |
| 6,364,888 B1 | 4/2002 | Niemeyer et al. | |
| 6,443,962 B1 | 9/2002 | Gaber | |
| 6,454,778 B2 | 9/2002 | Kortenbach | |
| 6,719,764 B1 | 4/2004 | Gellman et al. | |
| 6,743,239 B1 | 6/2004 | Kuehn et al. | |
| 6,783,524 B2 | 8/2004 | Anderson et al. | |
| 6,923,819 B2 | 8/2005 | Meade et al. | |
| 6,936,054 B2 | 8/2005 | Chu | |
| 6,939,358 B2 | 9/2005 | Palacios et al. | |
| 6,955,643 B2 | 10/2005 | Gellman et al. | |
| 7,004,951 B2 | 2/2006 | Gibbens, III | |
| 7,041,111 B2 | 5/2006 | Chu | |
| 7,131,979 B2 | 11/2006 | DiCarlo et al. | |
| 7,144,401 B2 | 12/2006 | Yamamoto et al. | |
| 7,232,447 B2 | 6/2007 | Gellman et al. | |
| 7,235,087 B2 | 6/2007 | Modesitt et al. | |
| 7,338,504 B2 | 3/2008 | Gibbens, III et al. | |
| 7,442,198 B2 | 10/2008 | Gellman et al. | |
| 7,491,166 B2 | 2/2009 | Ueno et al. | |
| 7,520,382 B2 | 4/2009 | Kennedy et al. | |
| 7,524,320 B2 | 4/2009 | Tierney et al. | |
| 7,582,096 B2 | 9/2009 | Gellman et al. | |
| 7,588,583 B2 | 9/2009 | Hamilton et al. | |
| 7,604,611 B2 | 10/2009 | Falwell et al. | |
| 7,615,060 B2 | 11/2009 | Stokes et al. | |
| 7,628,796 B2 | 12/2009 | Shelton, IV et al. | |
| 7,637,369 B2 | 12/2009 | Kennedy et al. | |
| 7,666,194 B2 | 2/2010 | Field et al. | |
| 7,686,831 B2 | 3/2010 | Stokes et al. | |
| 7,691,095 B2 | 4/2010 | Bednarek et al. | |
| 7,691,098 B2 | 4/2010 | Wallace et al. | |
| 7,703,653 B2 | 4/2010 | Shah et al. | |
| 7,763,036 B2 | 7/2010 | Stokes et al. | |
| 7,766,925 B2 | 8/2010 | Stokes et al. | |
| 7,806,891 B2 | 10/2010 | Nowlin et al. | |
| 7,815,654 B2 | 10/2010 | Chu | |
| 7,824,401 B2 | 11/2010 | Manzo et al. | |
| 7,828,812 B2 | 11/2010 | Stokes et al. | |
| 7,833,235 B2 | 11/2010 | Chu | |
| 7,833,236 B2 | 11/2010 | Stokes et al. | |
| 7,842,048 B2 | 11/2010 | Ma | |
| 7,846,169 B2 | 12/2010 | Shelton, IV et al. | |
| 7,862,572 B2 | 1/2011 | Meade et al. | |
| 7,862,582 B2 | 1/2011 | Ortiz et al. | |
| 7,887,554 B2 | 2/2011 | Stokes et al. | |
| 7,891,485 B2 | 2/2011 | Prescott | |
| 7,896,890 B2 | 3/2011 | Ortiz et al. | |
| 7,909,220 B2 | 3/2011 | Viola | |
| 7,935,128 B2 * | 5/2011 | Rioux et al. | 606/144 |
| 7,942,886 B2 | 5/2011 | Alvarado | |
| 7,947,052 B2 | 5/2011 | Baxter, III et al. | |
| 7,976,553 B2 | 7/2011 | Shelton, IV et al. | |
| 7,976,555 B2 | 7/2011 | Meade et al. | |
| 7,993,354 B1 | 8/2011 | Brecher et al. | |
| 8,012,161 B2 | 9/2011 | Primavera et al. | |
| 8,016,840 B2 | 9/2011 | Takemoto et al. | |
| 8,048,092 B2 | 11/2011 | Modesitt et al. | |
| 8,057,386 B2 | 11/2011 | Aznoian et al. | |
| 8,066,737 B2 | 11/2011 | Meade et al. | |
| 8,118,820 B2 | 2/2012 | Stokes et al. | |
| 8,123,762 B2 | 2/2012 | Chu et al. | |
| 8,123,764 B2 | 2/2012 | Meade et al. | |
| 8,136,656 B2 | 3/2012 | Kennedy et al. | |
| 8,187,288 B2 | 5/2012 | Chu et al. | |
| 8,196,739 B2 | 6/2012 | Kirsch | |
| 8,206,284 B2 | 6/2012 | Aznoian et al. | |
| 8,211,143 B2 | 7/2012 | Stefanchik et al. | |
| 8,236,010 B2 | 8/2012 | Ortiz et al. | |
| 8,236,013 B2 | 8/2012 | Chu | |
| 8,241,320 B2 | 8/2012 | Lyons et al. | |
| 8,246,637 B2 | 8/2012 | Viola et al. | |
| 8,252,008 B2 | 8/2012 | Ma | |
| 8,256,613 B2 | 9/2012 | Kirsch et al. | |
| 8,257,369 B2 | 9/2012 | Gellman et al. | |
| 8,257,371 B2 | 9/2012 | Hamilton et al. | |
| 8,292,067 B2 | 10/2012 | Chowaniec et al. | |
| 8,292,906 B2 | 10/2012 | Taylor et al. | |
| 8,361,089 B2 | 1/2013 | Chu | |
| 8,366,725 B2 | 2/2013 | Chu | |

(56) References Cited

U.S. PATENT DOCUMENTS

| | | |
|---|---|---|
| 8,372,090 B2 | 2/2013 | Wingardner et al. |
| 8,398,660 B2 | 3/2013 | Chu et al. |
| 8,460,320 B2 | 6/2013 | Hirzel |
| 8,469,973 B2 | 6/2013 | Meade et al. |
| 8,490,713 B2 | 7/2013 | Furnish et al. |
| 8,500,756 B2 | 8/2013 | Papa et al. |
| 8,512,243 B2 | 8/2013 | Stafford |
| 8,518,058 B2 | 8/2013 | Gellman et al. |
| 8,556,069 B2 | 10/2013 | Kirsch |
| 8,623,048 B2 | 1/2014 | Meade et al. |
| 8,641,728 B2 | 2/2014 | Stokes et al. |
| 8,696,687 B2 | 4/2014 | Gellman et al. |
| 8,702,729 B2 | 4/2014 | Chu |
| 8,709,021 B2 | 4/2014 | Chu et al. |
| 8,746,445 B2 | 6/2014 | Kennedy et al. |
| 8,747,304 B2 | 6/2014 | Zeiner et al. |
| 8,771,295 B2 | 7/2014 | Chu |
| 8,821,518 B2 | 9/2014 | Saliman et al. |
| 8,821,519 B2 | 9/2014 | Meade et al. |
| 2001/0025134 A1 | 9/2001 | Bon et al. |
| 2003/0208100 A1 | 11/2003 | Levy |
| 2004/0050721 A1 | 3/2004 | Roby et al. |
| 2005/0015101 A1 | 1/2005 | Gibbens, III et al. |
| 2005/0216038 A1 | 9/2005 | Meade et al. |
| 2006/0036232 A1 | 2/2006 | Primavera et al. |
| 2006/0282097 A1 | 12/2006 | Ortiz et al. |
| 2006/0282099 A1 | 12/2006 | Stokes et al. |
| 2007/0088372 A1 | 4/2007 | Gellman et al. |
| 2007/0173864 A1 | 7/2007 | Chu |
| 2008/0132919 A1 | 6/2008 | Chui et al. |
| 2008/0243146 A1 | 10/2008 | Sloan et al. |
| 2008/0255590 A1 | 10/2008 | Meade et al. |
| 2009/0088792 A1 | 4/2009 | Hoell, Jr. et al. |
| 2009/0205987 A1 | 8/2009 | Kennedy et al. |
| 2009/0209980 A1 | 8/2009 | Harris |
| 2009/0287226 A1 | 11/2009 | Gellman et al. |
| 2010/0023024 A1 | 1/2010 | Zeiner et al. |
| 2010/0042116 A1 | 2/2010 | Chui et al. |
| 2010/0063519 A1* | 3/2010 | Park et al. .................. 606/144 |
| 2010/0100125 A1 | 4/2010 | Mahadevan |
| 2011/0042245 A1 | 2/2011 | Mcclurg et al. |
| 2011/0046667 A1 | 2/2011 | Culligan et al. |
| 2011/0060352 A1 | 3/2011 | Chu |
| 2011/0288582 A1 | 11/2011 | Meade et al. |
| 2011/0313433 A1 | 12/2011 | Woodard et al. |
| 2012/0004672 A1 | 1/2012 | Giap et al. |
| 2012/0055828 A1 | 3/2012 | Kennedy et al. |
| 2012/0059396 A1 | 3/2012 | Harris et al. |
| 2012/0078243 A1 | 3/2012 | Worrell et al. |
| 2012/0123471 A1 | 5/2012 | Woodard et al. |
| 2012/0143248 A1 | 6/2012 | Brecher et al. |
| 2012/0150199 A1 | 6/2012 | Woodard et al. |
| 2012/0215234 A1 | 8/2012 | Chowaniec et al. |
| 2012/0220832 A1 | 8/2012 | Nakade et al. |
| 2012/0232567 A1 | 9/2012 | Fairneny |
| 2012/0283748 A1 | 11/2012 | Ortiz et al. |
| 2012/0283750 A1 | 11/2012 | Saliman et al. |
| 2012/0283755 A1 | 11/2012 | Gellman et al. |
| 2013/0041388 A1 | 2/2013 | Lane et al. |
| 2013/0158593 A1 | 6/2013 | Kiapour et al. |
| 2013/0282027 A1 | 10/2013 | Woodard et al. |
| 2013/0331866 A1 | 12/2013 | Gellman et al. |
| 2014/0088621 A1 | 3/2014 | Krieger et al. |
| 2014/0166514 A1 | 6/2014 | Martin et al. |
| 2014/0171970 A1 | 6/2014 | Martin et al. |
| 2014/0171971 A1 | 6/2014 | Martin et al. |
| 2014/0171972 A1 | 6/2014 | Martin |
| 2014/0171975 A1 | 6/2014 | Martin et al. |
| 2014/0171976 A1 | 6/2014 | Martin et al. |
| 2014/0171977 A1 | 6/2014 | Martin et al. |
| 2014/0171978 A1 | 6/2014 | Martin |
| 2014/0171979 A1 | 6/2014 | Martin et al. |
| 2014/0172015 A1 | 6/2014 | Martin et al. |

FOREIGN PATENT DOCUMENTS

| | | |
|---|---|---|
| EP | 0739184 B1 | 9/1998 |
| EP | 1791476 | 6/2007 |
| EP | 2292157 | 3/2011 |
| EP | 2308391 | 4/2011 |
| FR | 2540377 | 2/1984 |
| GB | 190818602 | 0/1909 |
| GB | 2389313 | 12/2003 |
| JP | 55-151956 | 11/1980 |
| WO | WO 95/19149 | 7/1995 |
| WO | WO 97/29694 | 8/1997 |
| WO | WO 99/12482 | 3/1999 |
| WO | WO 99/40850 | 8/1999 |
| WO | WO 99/47050 | 9/1999 |
| WO | WO 01/12084 | 2/2001 |
| WO | WO 02/102226 | 12/2002 |
| WO | WO 03/028541 | 4/2003 |
| WO | WO 2004/012606 | 2/2004 |
| WO | WO 2004/021894 | 3/2004 |
| WO | WO 2006/034209 | 3/2006 |
| WO | WO 2007/089603 | 8/2007 |
| WO | WO 2008/045333 | 4/2008 |
| WO | WO 2008/045376 | 4/2008 |
| WO | WO 2008/147555 | 12/2008 |
| WO | WO 2010/062380 | 6/2010 |
| WO | WO 2012/044998 | 4/2012 |

OTHER PUBLICATIONS

U.S. Appl. No. 61/413,680, filed Nov. 15, 2010.
Covidien Brochure Endo Stitch, Suturing Made Easy Features and Benefits, 2008, 4 pages.
Endoevolution, LLC, Endo 360, Laparoscopic & Minimally Invasive Suturing Devices Catalog, 2011, 2 pages.
Endoevolution, LLC, Endo 360, Laparoscopic & Minimally Invasive Suturing Devices Catalog 2013, 10 pages.

* cited by examiner

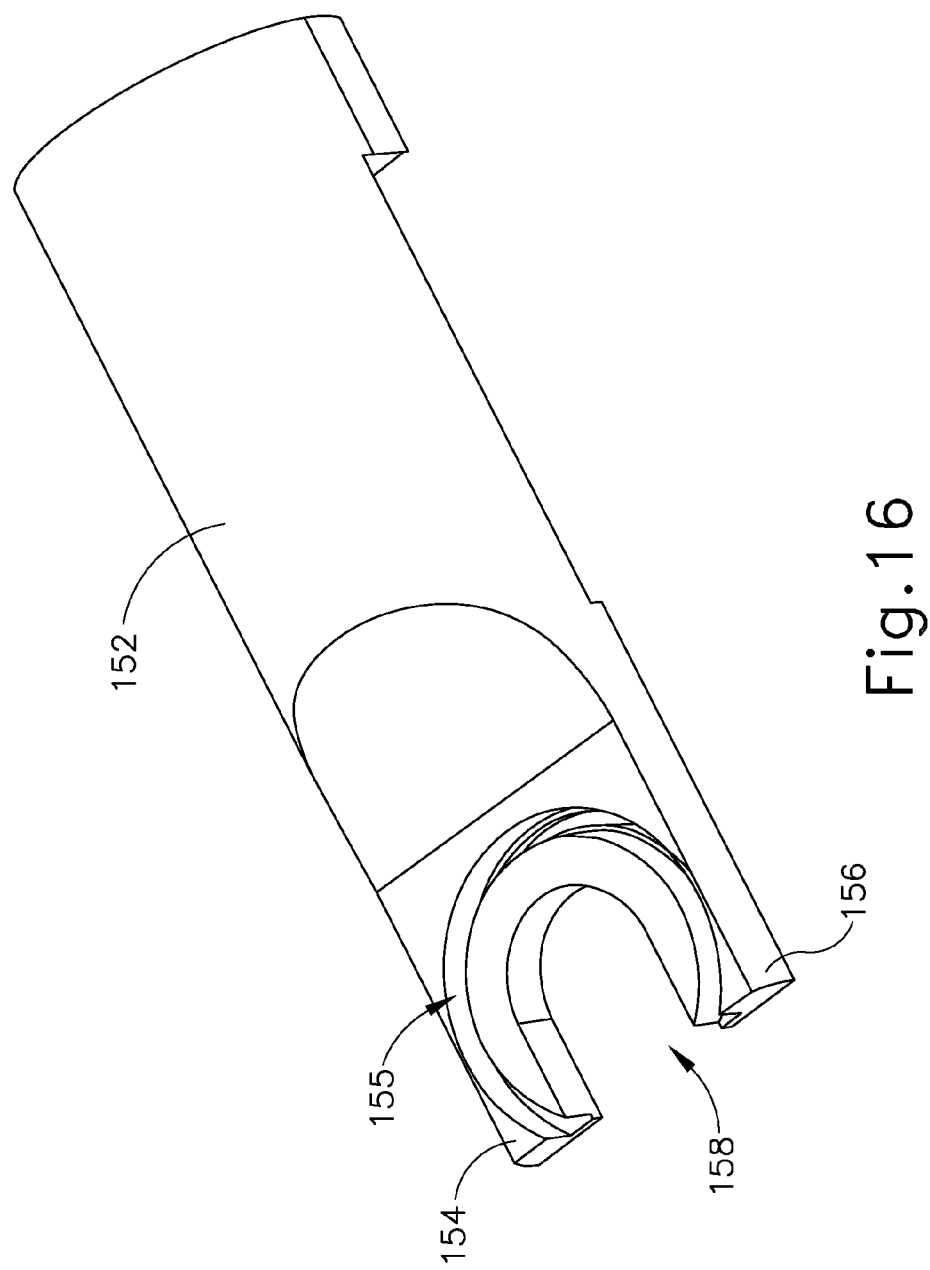

RECIPROCATING NEEDLE DRIVE WITHOUT CABLES

BACKGROUND

In some settings it may be desirable to perform a surgical procedure in a minimally invasive manner, such as through a trocar or other type of access cannula. Examples of trocars include the various ENDOPATH® EXCEL™ products by Ethicon Endo-Surgery, Inc. of Cincinnati, Ohio. Such trocars may present different inner diameters, such as those ranging from approximately 4.7 mm to approximately 12.9 mm, allowing a surgeon to choose a particular trocar based on a balance of considerations such as access needs and incision size. In some minimally invasive surgical procedures, at least two trocars may be inserted through the abdominal wall of the patient. An imaging device such as an endoscope may be inserted through one of the trocars to provide visualization of the surgical site. A surgical instrument may be inserted through another one of the trocars to perform surgery at the site. In procedures performed within the abdominal cavity, the cavity may be insufflated with pressurized carbon dioxide to provide more room for visualization and manipulation of instruments. In some settings, additional trocars may be used to provide access for additional surgical instruments. Minimally invasive surgery may also be performed through access portals such as the Single Site Laparoscopy Access System by Ethicon Endo-Surgery, Inc. of Cincinnati, Ohio, which provides ports for more than one surgical instrument through a single incision in a patient.

It may also be desirable to use sutures during some minimally invasive surgical procedures, such as to close an opening, to secure two layers of tissue together, to provide an anastomosis, etc. Such use of sutures may be in addition to or in lieu of using other devices and techniques such as clips, staples, electrosurgical sealing, etc. Performing suturing through trocars or other minimally invasive access ports may be more difficult than suturing in an open surgical procedure. For instance, manipulating a needle and suture with conventional tissue graspers through trocars may be relatively difficult for many surgeons. Thus, improved laparascopic surgical instruments may make suturing procedures performed through trocars relatively easier. Examples of surgical instruments configured to facilitate suturing through trocars include the LAPRA-TY® Suture Clip Applier, the Suture Assistant, and the ENDOPATH® Needle Holder, all of which are by Ethicon Endo-Surgery, Inc. of Cincinnati, Ohio.

Additional suturing instruments are disclosed in U.S. Pat. No. 5,437,681, entitled "Suturing Instrument with Thread Management," issued Aug. 1, 1995, the disclosure of which is incorporated by reference herein; U.S. Pat. No. 5,540,706, entitled "Surgical Instrument," issued Jul. 30, 1996, the disclosure of which is incorporated by reference herein; U.S. Pat. No. 6,923,819, entitled "Apparatus and Method for Surgical Suturing with Thread Management," issued Aug. 2, 2005, the disclosure of which is incorporated by reference herein; U.S. Pat. No. 6,071,289, entitled "Surgical Device for Suturing Tissue," issued Jun. 6, 2000, the disclosure of which is incorporated by reference herein; U.S. Pat. No. 7,628,796, entitled "Surgical Suturing Apparatus with Anti-Backup System," issued Dec. 8, 2009, the disclosure of which is incorporated by reference herein; U.S. Pat. No. 7,862,572, entitled "Apparatus and Method for Minimally Invasive Suturing," issued Jan. 4, 2011, the disclosure of which is incorporated by reference herein; U.S. Pat. No. 7,976,555, entitled "Apparatus and Method for Minimally Invasive Suturing," issued Jul. 12, 2011, the disclosure of which is incorporated by reference herein; U.S. Pub. No. 2011/0313433, entitled "Laparoscopic Suture Device with Asynchronous In-Line Needle Movement," filed Jun. 9, 2011, the disclosure of which is incorporated by reference herein; U.S. patent application Ser. No. 13/449,494, entitled "Laparoscopic Suturing Instrument with parallel Concentric Shaft Pairs," filed Apr. 18, 2012, and published Oct. 24, 2013 as U.S. Pub. No. 2013/0282027, the disclosure of which is incorporated by reference herein; and U.S. Provisional Patent Application No. 61/355,832, entitled "Laparoscopic Suture Device," filed Jun. 17, 2010, the disclosure of which is incorporated by reference herein.

Exemplary suturing needles are disclosed in U.S. Pat. No. 6,056,771, entitled "Radiused Tip Surgical Needles and Surgical Incision Members," issued May 2, 2000, the disclosure of which is incorporated by reference herein; U.S. Pub. No. 2010/0100125, entitled "Suture Needle and Suture Assembly," published Apr. 22, 2010, the disclosure of which is incorporated by reference herein; U.S. Provisional Application Ser. No. 61/413,680, filed Nov. 15, 2010, entitled "Custom Needle for Suture Instrument," the disclosure of which is incorporated by reference herein; U.S. patent application Ser. No. 13/295,186, entitled "Needle for Laparoscopic Suturing Instrument," filed on Nov. 14, 2011, and published May 17, 2012 as U.S. Pub. No. 2012/0123471, the disclosure of which is incorporated by reference herein; and U.S. patent application Ser. No. 13/295,203, entitled "Laparoscopic Suturing Instrument with Dual-Action Needle Graspers," filed on Nov. 14, 2011, and issued Apr. 22, 2014 as U.S. Pat. No. 8,702,732, the disclosure of which is incorporated by reference herein.

While a variety of devices and methods have been made and used for suturing tissue, it is believed that no one prior to the inventor(s) has made or used the technology described herein.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 16 depicts a perspective view of a cover of the end effector of FIG. 8;

Figure 1:
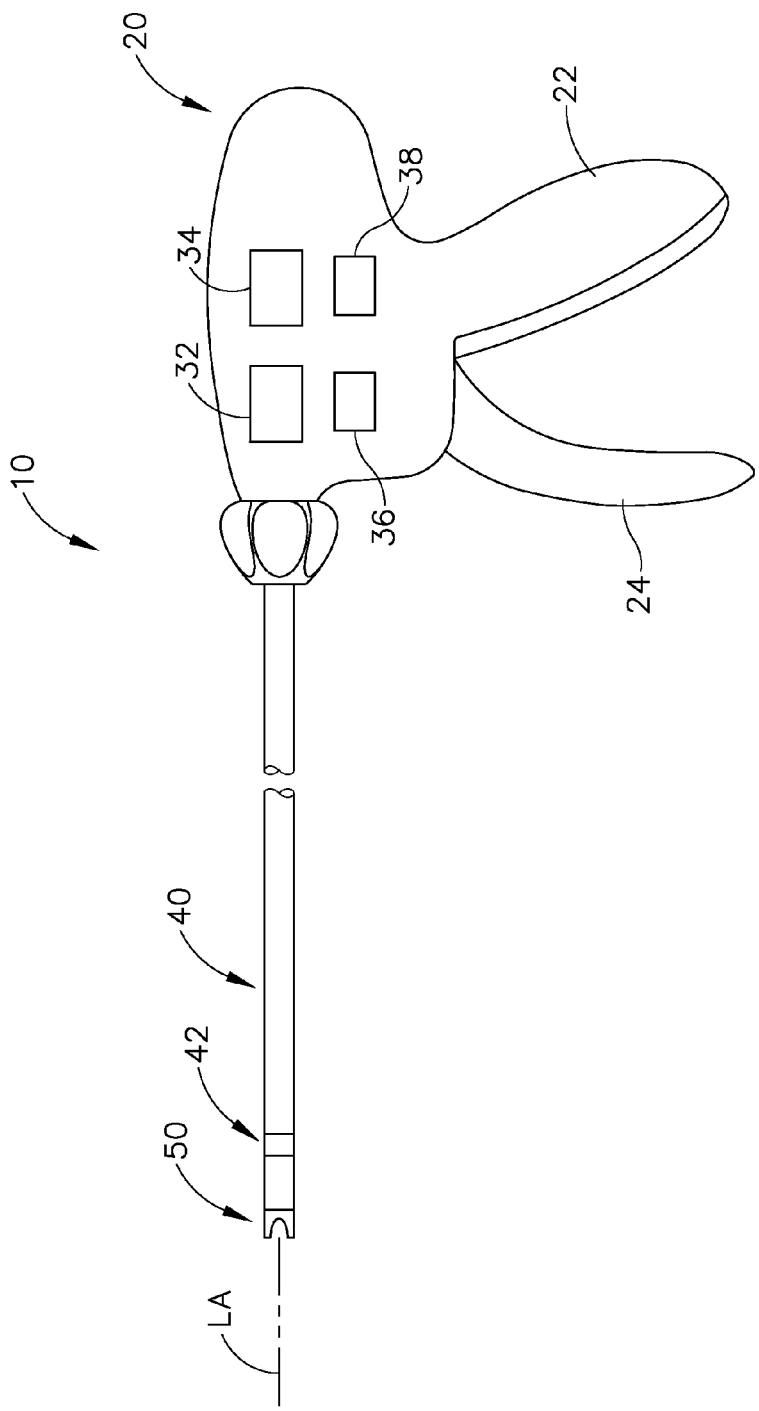
FIG. 1 depicts a schematic elevational view of an exemplary suturing instrument.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It should therefore be understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. Exemplary Suturing Instrument

FIG. 1 shows an exemplary laparoscopic suturing instrument (10), which may be used to suture tissue in numerous kinds of surgical procedures. Instrument (10) of this example includes a handle portion (20), a shaft (40) extending distally from handle portion (20), and an end effector (50) that is joined to shaft (40) by a joint (42). Handle portion (20) includes a grip (22) and a trigger (24), which is pivotable relative to grip (22) to actuate end effector (50) as will be described in greater detail below. In some versions, shaft (40) and end effector (50) are configured to fit through a conventional trocar. It should therefore be understood that instrument (10) may be used in minimally invasive procedures. Of course, instrument (10) may be used through passageways other than trocars (e.g., through a thoracotomy, etc.) or in open procedures if desired.

In the present example, shaft (40) is rotatable to position end effector (50) at various angular orientations about the longitudinal axis (LA) defined by shaft (40). To that end, handle portion (20) includes a rotation control (32). It should be understood that rotation control (32) may take a variety of forms, including but not limited to a knob, a dial, a grip at the proximal end of shaft (40), etc. Various suitable forms that rotation control (32) may take will be apparent to those of ordinary skill in the art in view of the teachings herein. In addition to providing rotation of end effector (50), instrument (10) also provides articulation of end effector (50). In particular, joint (42) at the distal end of shaft (40) enables end effector (50) to pivotally deflect away from the longitudinal axis (LA) defined by shaft (40) to achieve various articulation angles. It should be understood that these various articulation angles may be achieved at any of the various angular orientations provided through rotation control (32). Handle portion (20) further includes an articulation control (34), which may include any suitable component such as a knob, a dial, a lever, a slider, etc. Various suitable forms that articulation control (34) may take will be apparent to those of ordinary skill in the art in view of the teachings herein. Similarly, various suitable components and configurations that may be used to provide articulation of end effector (50) at joint (42) in response to actuation of articulation control (34) will be apparent to those of ordinary skill in the art in view of the teachings herein. By way of example only, articulation may be provided in accordance with at least some of the teachings of U.S. Pat. No. 7,862,572, the disclosure of which is incorporated by reference herein.

In some versions, handle portion (20) includes a powered motive source (36). Powered motive source (36) may comprise a motor, a solenoid, and/or any other suitable type of powered motive source. Powered motive source (36) may be used to drive end effector (50) as will be described in greater detail below, to rotate shaft (40), to articulate end effector (50) at joint (42), and/or to provide any other suitable type of operation. It should also be understood that handle portion (20) may include an integral power source (38). By way of example only, integral power source (38) may comprise a rechargeable battery coupled with powered motive source (36). Alternatively, in versions of instrument (10) where at least one component receives electrical power, such electrical power may be provided by an external source that is coupled with instrument (10) via wire, via inductive coupling, or otherwise. It should be understood that versions of instrument (10) having powered motive source (36) and/or integral power source (38) may have additional associated components, including but not limited to transmission components, clutch components, sensors, a control module, etc. Various suitable components and combinations thereof will be apparent to those of ordinary skill in the art in view of the teachings herein. It should also be understood that instrument (10) may simply lack powered motive source (36) and/or power source (38).

Figure 2:
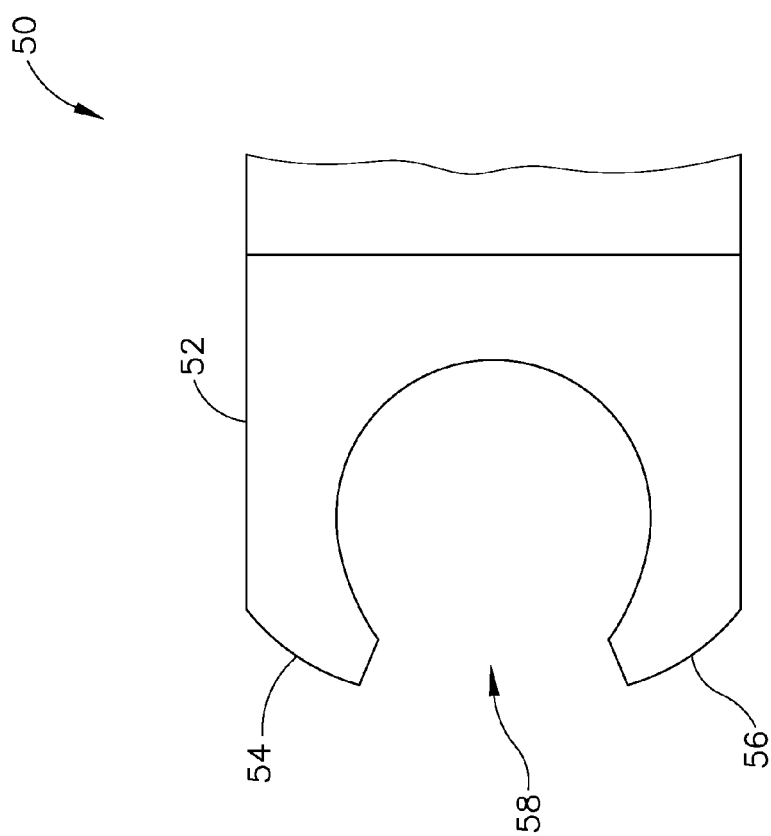
FIG. 2 depicts an enlarged partial elevational view of the end effector of the suturing instrument of FIG. 1.
Figure 3:
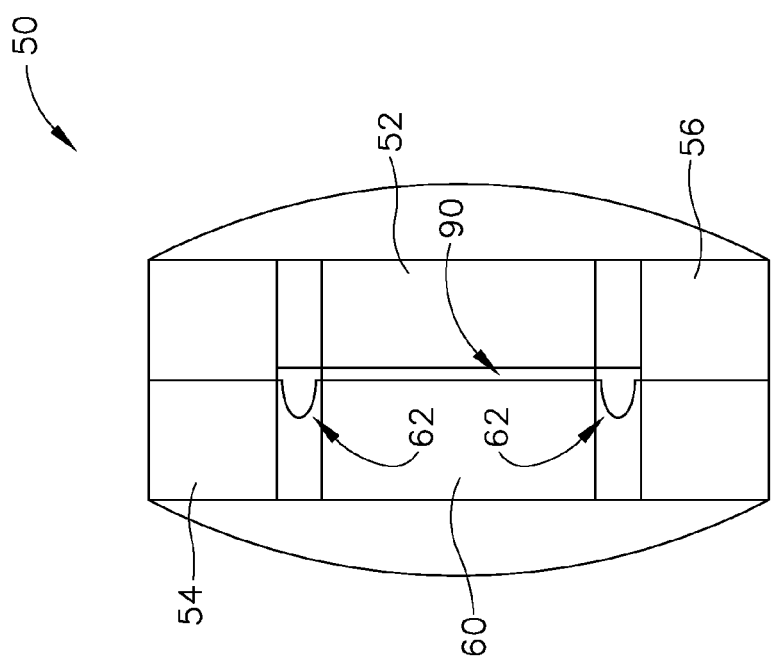
FIG. 3 depicts an end view of the end effector of FIG. 2.
Figure 5:
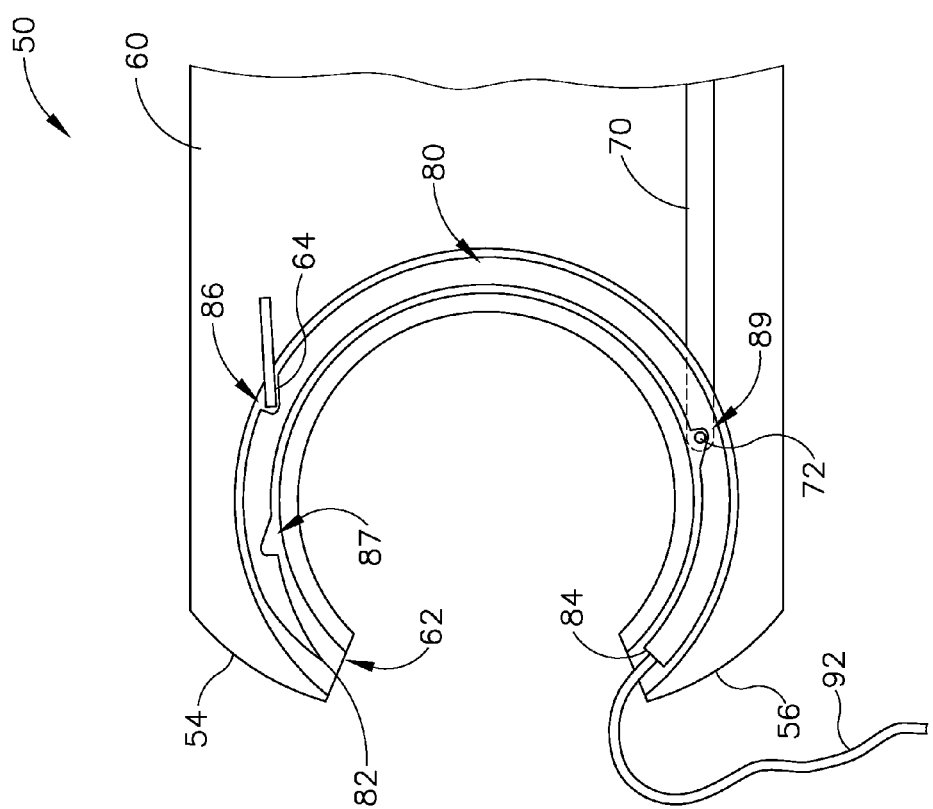
FIG. 5 depicts an enlarged partial elevational view of the needle of FIG. 4 loaded in the end effector of FIG. 2, with a cover of the end effector removed.

FIGS. 2-3 and 5 show end effector (50) of the present example in greater detail. In particular, end effector (50) of the present example comprises a cover (52), a frame base (60), a needle exit arm (54), and a needle entry arm (56). Arms (54, 56) define a gap (58) for receiving tissue, with end effector (50) being operable to drive a needle (80) with suture (92) through the tissue received in gap (58). Frame base (60) defines a curved channel (62) that terminates at the free end of each arm (54, 56) and that is sized to receive a curved needle (80). Cover (52) is movable relative frame base (60) to selectively cover and uncover channel (62) with needle (80) contained therein. By way of example only, cover (52) may slide proximally relative to frame base (60) to selectively uncover channel (62) and needle (80); and distally relative to frame base (60) to selectively cover channel (62) and needle (80). In some other versions, cover (52) may snap on and off of frame base (60), may pivot toward and away from frame base (60), or be movable in some other fashion. It should also be understood that cover (52) may be movable relative to frame base (60) in accordance with at least some of the teachings of U.S. Pat. No. 7,862,572, the disclosure of which is incorporated by reference herein and/or U.S. Pat. No. 7,976,555, the disclosure of which is incorporated by reference herein. As can be seen in FIG. 3, even when cover (52) is positioned over frame base (60) to cover frame base (60) and needle (80), cover (52) and frame base (60) define a gap (90) that is configured to enable suture (92) to travel through gap (90) as needle (80) is being driven along a circular path as described below, thereby preventing suture (92) from getting stuck in channel (62).

Figure 4:
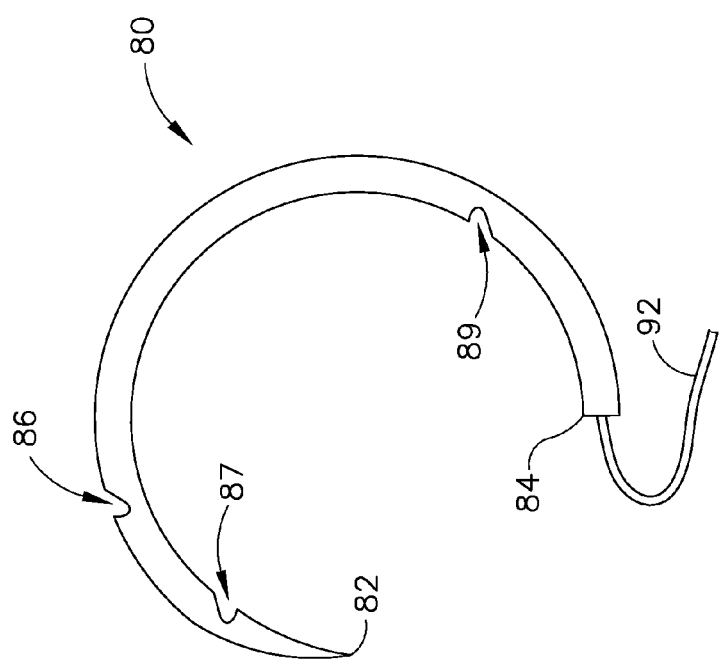
FIG. 4 depicts an elevational view of an exemplary needle suited for use with the suturing instrument of FIG. 1.

As shown in FIG. 4, needle (80) of the present example is curved, forming an incomplete circle. Needle (80) includes a sharp tip (82) and a blunt end (84). In the present example, the body of needle (80) extends along a portion of a circle along approximately 270°, though it should be understood that needle (80) may instead extend through any other suitable angular extent. Sharp tip (82) is configured to pierce tissue repeatedly as needle (80) makes multiple passes through tissue. Suture (92) is integrally secured to the blunt end (84) of needle. Needle (80) is includes an anti-backup notch (86), a needle return notch (87), and a needle drive notch (89). These notches (86, 87, 89) interact with complementary features of end effector (50) as will be described in greater detail below. By way of example only, at least part of needle (80) may be constructed in accordance with at least some of the teachings of U.S. Pub. No. 2012/0123471, entitled "Needle for Laparoscopic Suturing Instrument," published May 17, 2012, the disclosure of which is incorporated by reference herein, U.S. Pat. No. 7,862,572, the disclosure of which is incorporated by reference herein and/or U.S. Pat. No. 7,976,555, the disclosure of which is incorporated by reference herein.

As shown in FIG. 5, frame base (60) further includes a pawl (64) and a drive arm (70), which has a drive pin (72). Pawl (64) extends distally and has a free end configured to fit in anti-backup notch (86) of needle (80) when needle (80) is in a home position. Pawl (64) is resiliently biased to extend distally but is further configured to deflect laterally when needle (80) is being driven. By way of example only, pawl (64) may comprise a resilient strip of metal that is integrally secured in frame base (60). As another merely illustrative example, pawl (64) may comprise a rigid member that is pivotally secured to frame base (60) and spring-loaded to provide a resilient bias to the position shown in FIG. 5. Various other suitable configurations for pawl (64) will be apparent to those of ordinary skill in the art in view of the teachings herein. Drive pin (72) is configured to fit in needle return notch (87) and in needle drive notch (89). Drive arm (70) is movable to move pin (72) along a circular path, to thereby drive needle (80) along a circular path. Drive arm (70) may move in response to pivoting of trigger (24) toward grip (22), in response to activation of powered motive source (36), or in response to any other suitable type of input. It should be understood that various types of components and assemblies may be employed to actuate drive arm in response to a user input. By way of example only, such components and assemblies may be constructed in accordance with at least some of the teachings of U.S. Pat. No. 7,862,572, the disclosure of which is incorporated by reference herein. Still other suitable components and assemblies that may be employed to drive arm (70) will be apparent to those of ordinary skill in the art in view of the teachings herein.

Figure 6A:
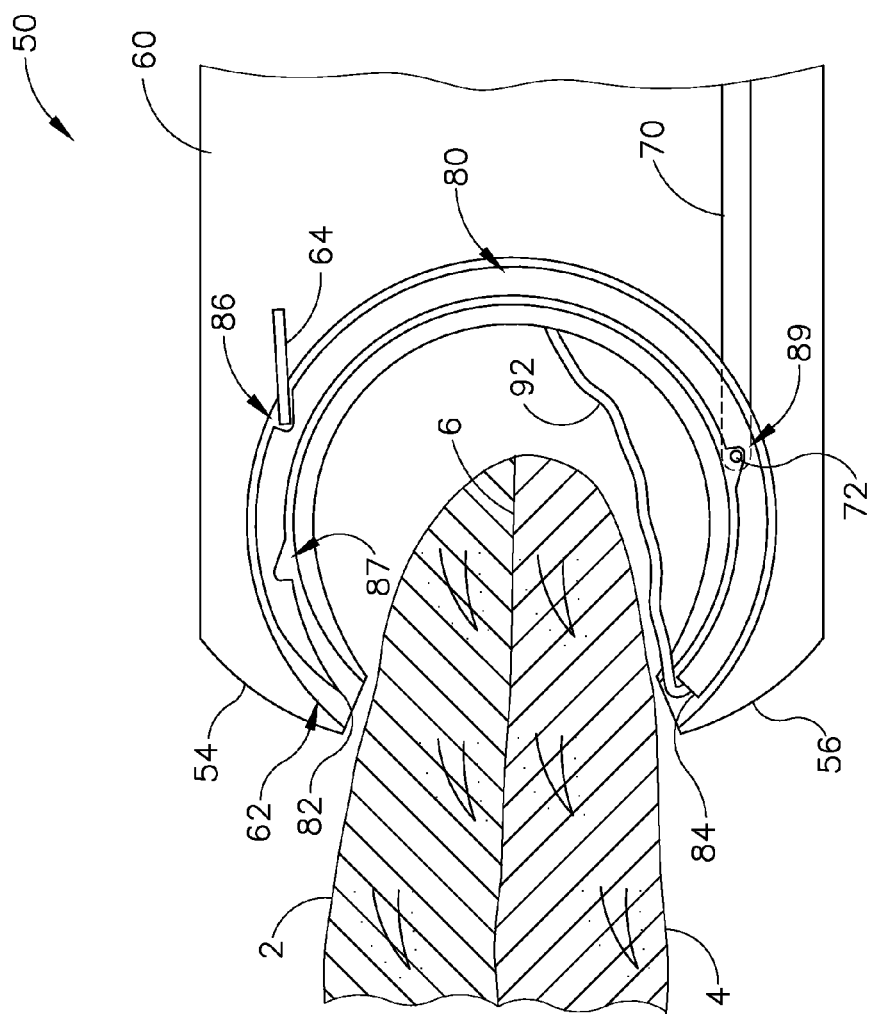
FIG. 6A depicts an enlarged partial elevational view of the loaded end effector of FIG. 5, with the end effector positioned about tissue.
Figure 6B:
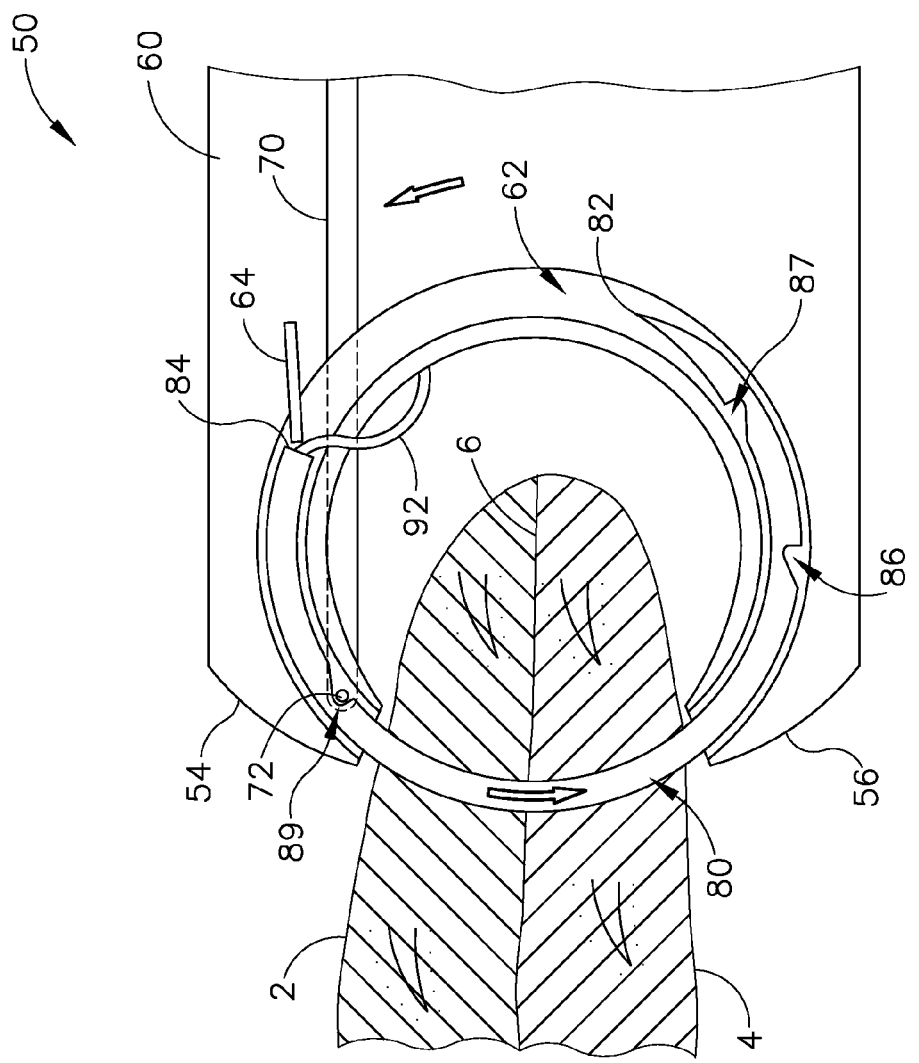
FIG. 6B depicts an enlarged partial elevational view of the loaded end effector of FIG. 5, with the end effector driving the needle through the tissue.

FIGS. 6A-6E show exemplary stages of use of end effector (50) to securely close an incision (6) that splits two layers (2, 4) of tissue. In some uses, end effector (50) is used to simply close an incision (6) that was formed by cutting a single planar layer of tissue with a cutting instrument in a single anatomical structure, with two apposed layers (2, 4) being formed by folding and pinching together the single layer in order to engage end effector (50). In some other uses, end effector (50) is used to suture a layer (2) of tissue of one anatomical structure to a layer (4) of tissue of another anatomical structure. Other suitable contexts for using end effector (50) will be apparent to those of ordinary skill in the art in view of the teachings herein. As shown in FIG. 6A, layers (2, 4) are positioned in gap (58) between arms (54, 56). By way of example only, layers (2, 4) may be manipulated using a set of conventional tissue graspers and/or any other suitable instrumentation to position layers (2, 4) in gap (58). With layers (2, 4) suitably positioned, drive arm (70) is actuated as shown in FIG. 6B to drive needle (80) along a circular path (counterclockwise in the views shown in FIGS. 6A-6E). The orbital motion of arm (70) is transferred to needle (80) via pin (72) in needle drive notch (89). This orbital motion drives needle (80) approximately 180° along a circular path. During this travel, tip (82) pierces both layers (2, 4) of tissue, such that needle (80) is disposed in both layers (2, 4) of tissue.

Figure 6C:
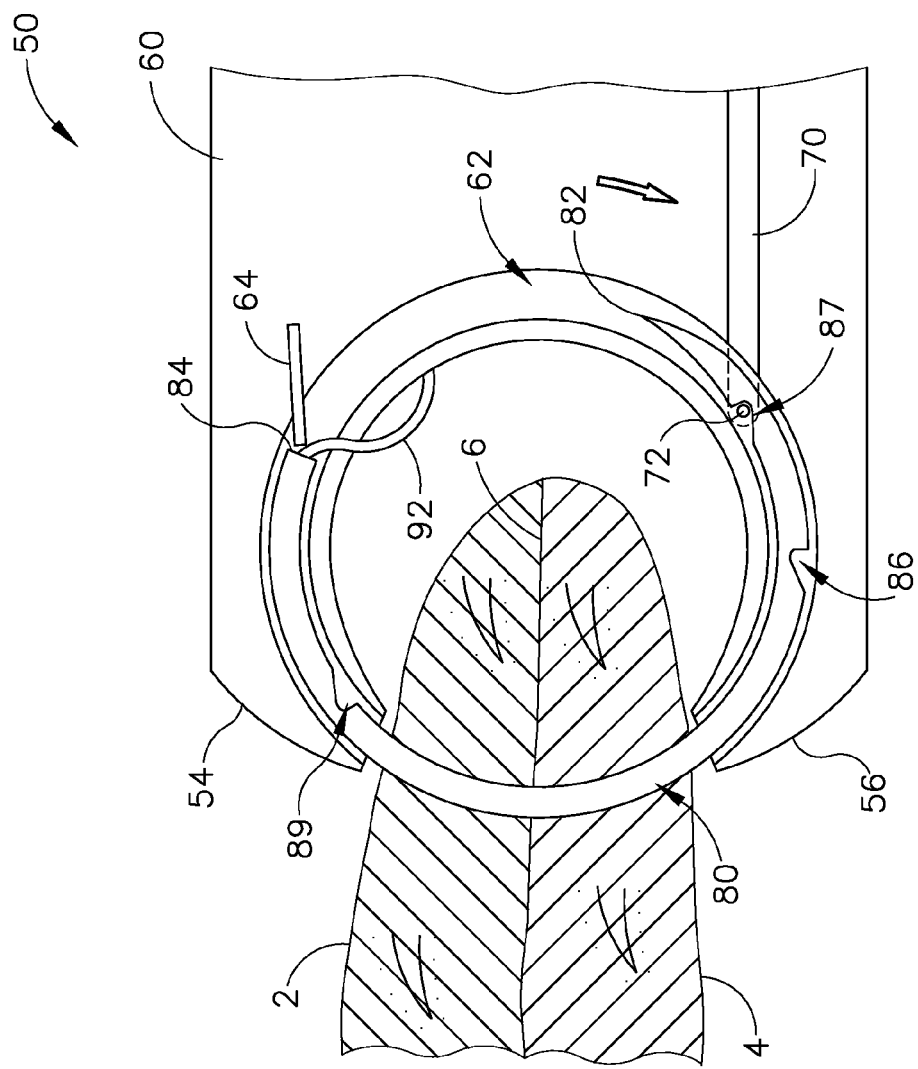
FIG. 6C depicts an enlarged partial elevational view of the loaded end effector of FIG. 5, with the end effector resetting a needle driver.
Figure 6D:
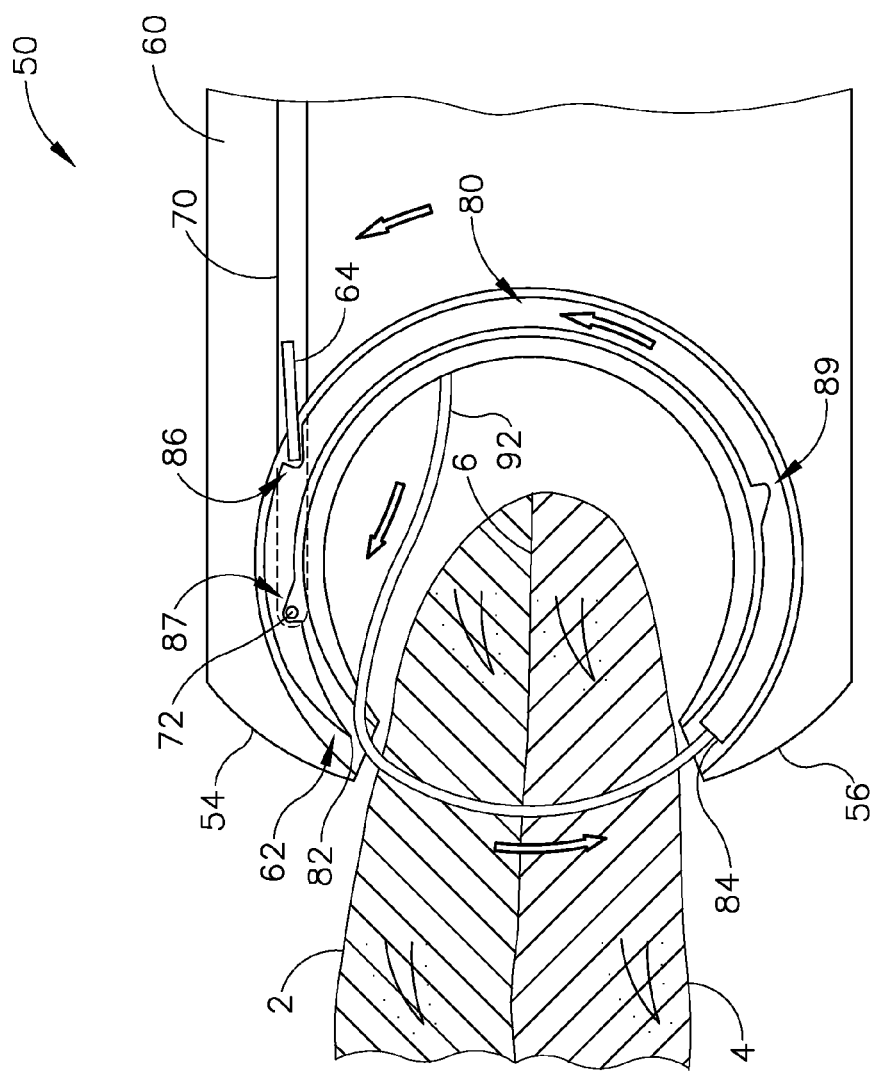
FIG. 6D depicts an enlarged partial elevational view of the loaded end effector of FIG. 5, with the end effector completing a pass of the needle through the tissue, thereby drawing suture through the tissue.

As shown in FIG. 6B, suture (92) has been pulled due to needle (80) being driven along the circular path through channel (62). However, suture (92) does not completely follow needle (80) along the path through channel (62). Instead, suture (92) travels through (90) gap. This allows suture (92) to avoid getting repeatedly wrapped through channel (62) as needle (80) is repeatedly driven through channel (62). As also shown in FIG. 6B, the free end of pawl (64) is positioned behind blunt end (84) of needle (80) at this stage. This prevents needle (80) from traveling in reverse (clockwise in the views shown in FIGS. 6A-6E) as drive arm (70) is returned to the home position as shown in FIG. 6C. When drive arm (70) is driven from the actuated position (FIG. 6B) back to the home position (FIG. 6C), pin (72) pivots away from needle (80) and out of engagement with needle drive notch (89). By way of example only, pin (72) may selectively disengage notch (89) in accordance with at least some of the teachings of U.S. Pat. No. 7,862,572, the disclosure of which is incorporated by reference herein. Still other suitable ways in which pin (72) may selectively disengage notch (89) for return of arm (70) to the home position will be apparent to those of ordinary skill in the art in view of the teachings herein.

With arm (70) to the home position as shown in FIG. 6C, pin (72) is disposed in needle return notch (87). This enables arm (70) to continue driving needle (80) along the circular path, to the position shown in FIG. 6D. In this position, needle (80) has returned to the same home position previously shown in FIG. 6A, such that needle (80) has been completely pulled through both layers (2, 4) of tissue. Needle (80) has thus traveled through a full 360° circular orbital path at this stage, and has thereby completed a full drive stroke. This further results in needle (80) pulling suture (92) through both layers (2, 4) of tissue. Pawl (64) is once again disposed in anti-backup notch (86), again preventing reversal of needle (80). Arm (70) is then again moved back to the home position, with pin (72) disengaging needle return notch (87) in the same manner as the disengagement of pin (72) from needle drive notch (89) as described above.

Figure 6E:
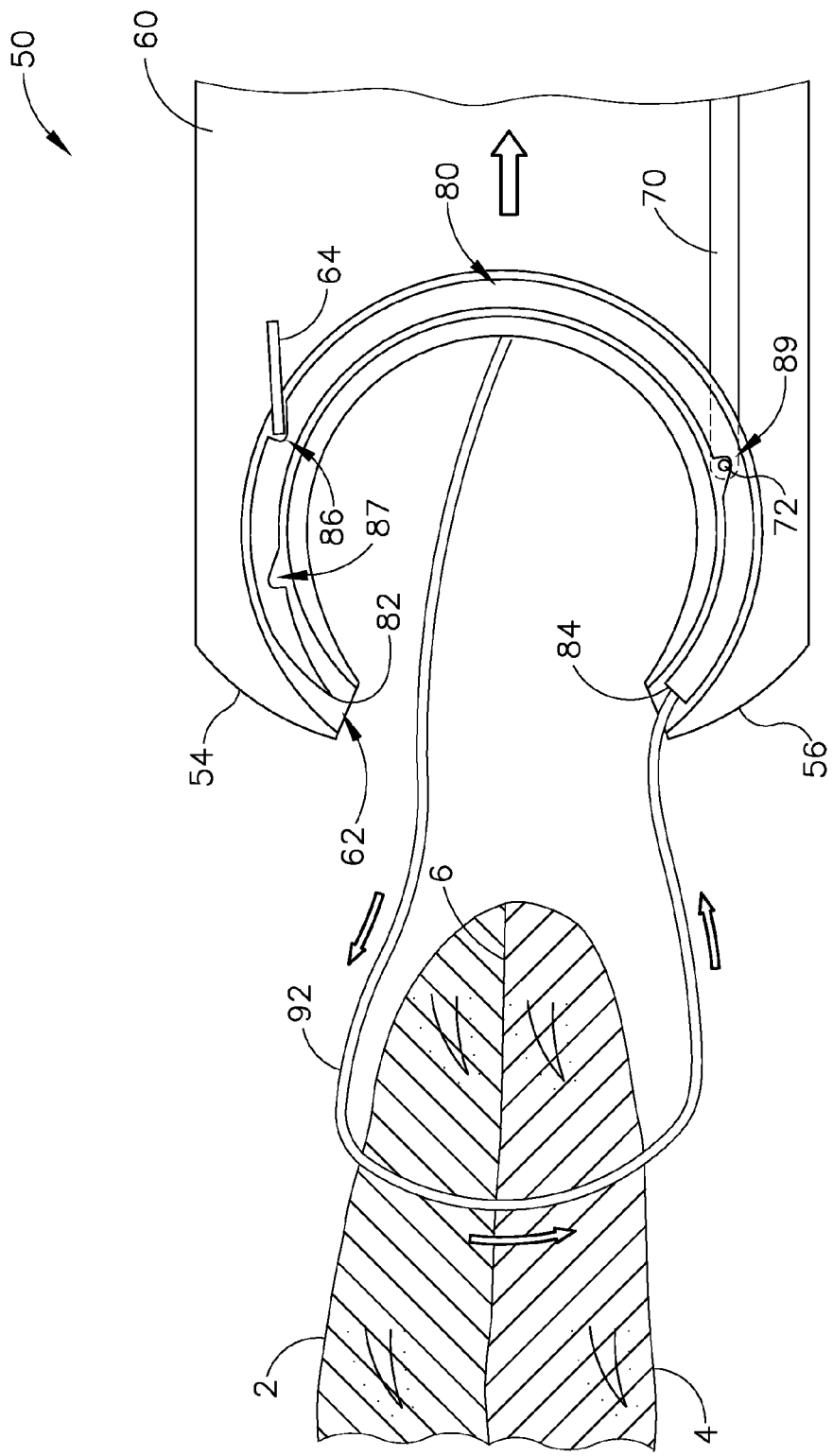
FIG. 6E depicts an enlarged partial elevational view of the loaded end effector of FIG. 5, with the end effector being pulled away from the tissue to pull additional suture through the tissue.
Figure 7:
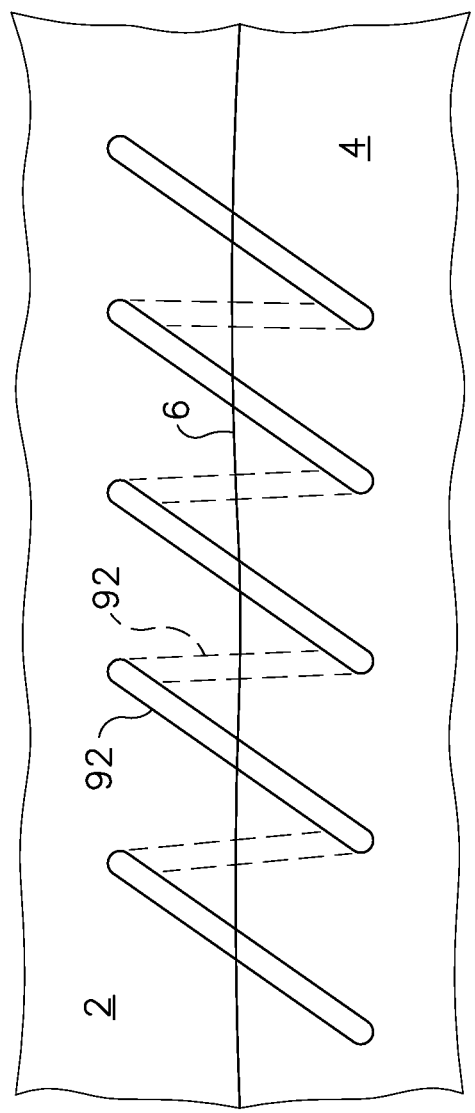
FIG. 7 depicts a top plan view of tissue sutured using the instrument of FIG. 1.

With arm (70) being returned to the home position, the entire end effector (50) is then pulled away from layers (2, 4) of tissue to draw suture (92) through layers (2, 4) of tissue as shown in FIG. 6E. To the extent that this creates tension on suture (92) that might urge needle (80) to back out through channel (62), engagement between pawl (64) and anti-backup notch (86) prevents such backing out of needle (80). After pulling additional length of suture (92) through layers (2, 4) of tissue as shown in FIG. 6E, end effector (50) may be moved to another position along incision (6), with layers (2, 4) being repositioned in gap (58), such that the process shown in FIGS. 6A-6E may be repeated any number of times as desired to create a series of stitches along incision (6). The resulting stitches may appear similar to what is shown in FIG. 7. As shown, the portion of suture (92) disposed within layers (2, 4) of tissue is oriented generally transversely to the line defined by incision (60); while the portion of suture (92) that is external to layers (2, 4) of tissue is oriented obliquely relative to the line defined by incision (60). Of course, suture (92) may instead have any other types of configurations after being passed through layers (2, 4) of tissue to form a series of stitches. Other suitable ways in which instrument (10) may be used will be apparent to those of ordinary skill in the art in view of the teachings herein.

II. Exemplary Suturing Instrument with a Drive Gear Assembly

Figure 8:
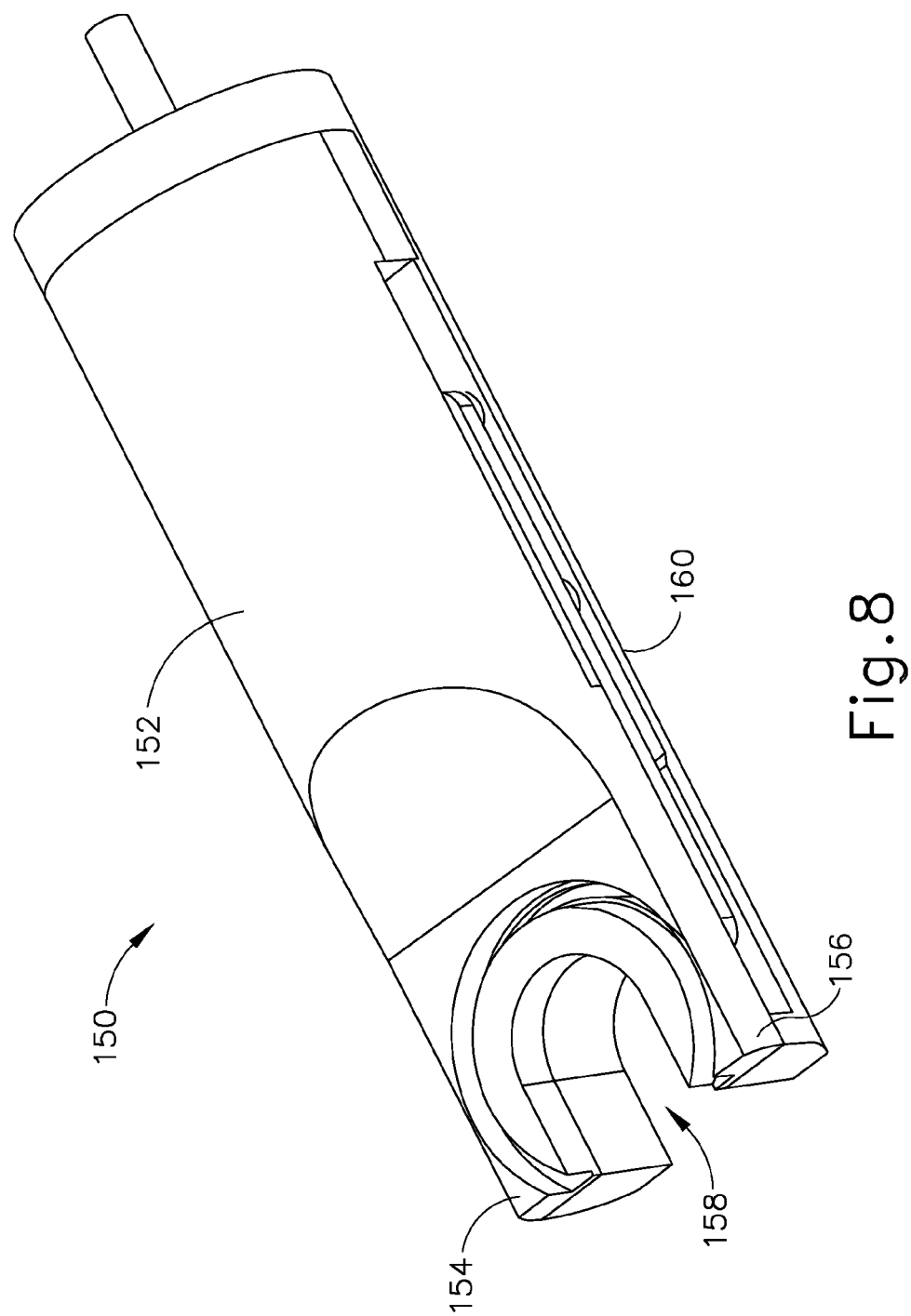
FIG. 8 depicts a perspective view of another exemplary end effector for use with the instrument of FIG. 1.

FIG. 8 shows another exemplary end effector (150). End effector (150) is similar to end effector (50) described above in that end effector (150) has a cover (152), a frame base (160), a needle exit arm (154), and a needle entry arm (156) that are similar to cover (52), frame base (60), needle exit arm (54), and needle entry arm (56) described above. However, end effector (150) of this example is different from end effector (50) in that end effector (150) comprises a drive gear assembly to drive needle (80) through end effector (150). The examples below include several merely illustrative versions of drive gear assembly features that may be readily introduced to an instrument (10).

Figure 9:
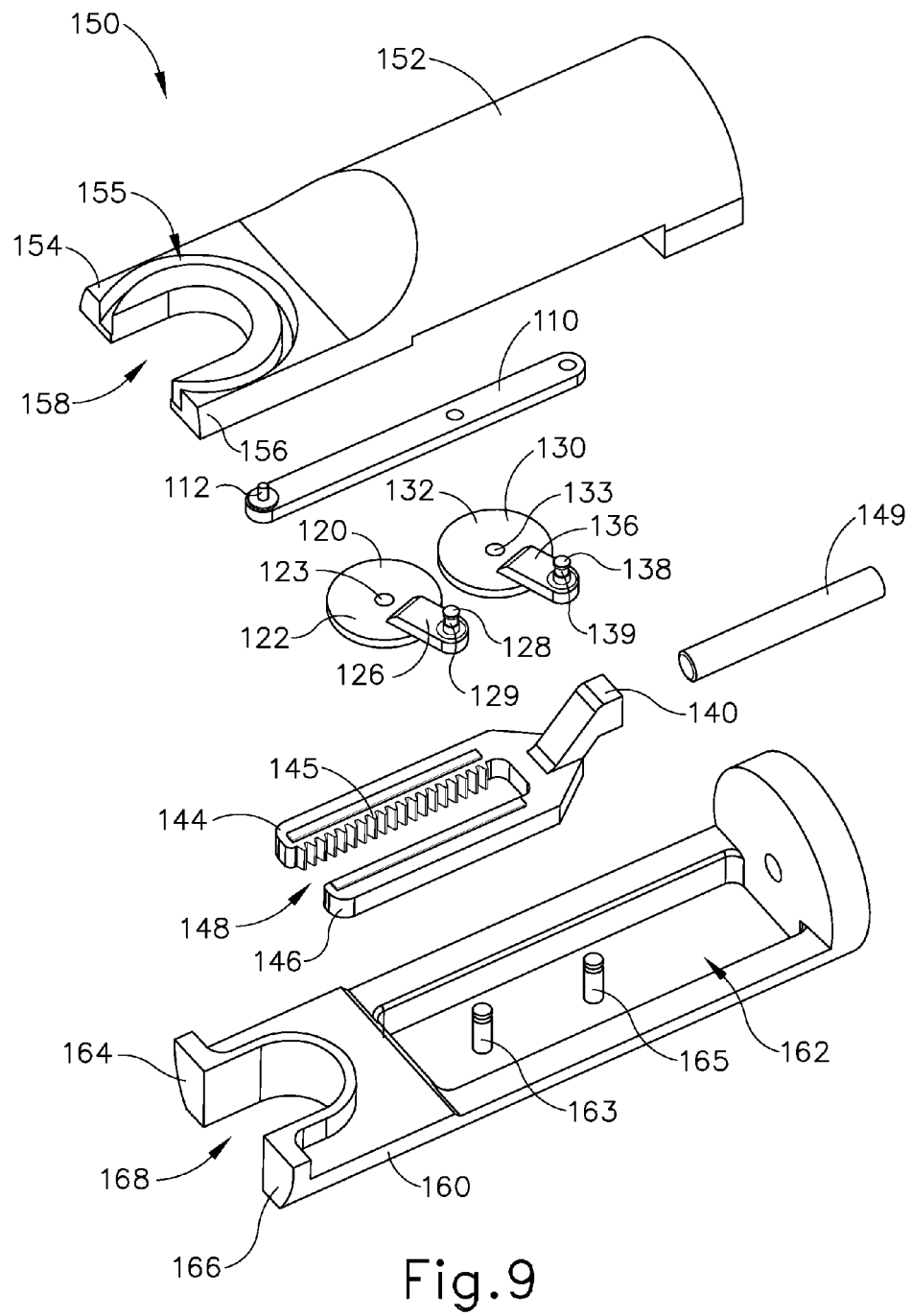
FIG. 9 depicts an exploded view of the end effector of FIG. 8.
Figure 10:
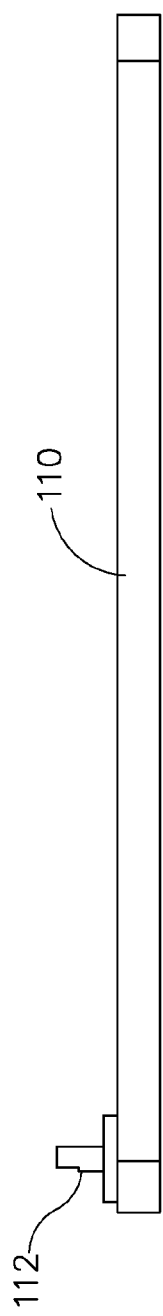
FIG. 10 depicts a side elevational view of a drive arm of the end effector of FIG. 8.
Figure 11:
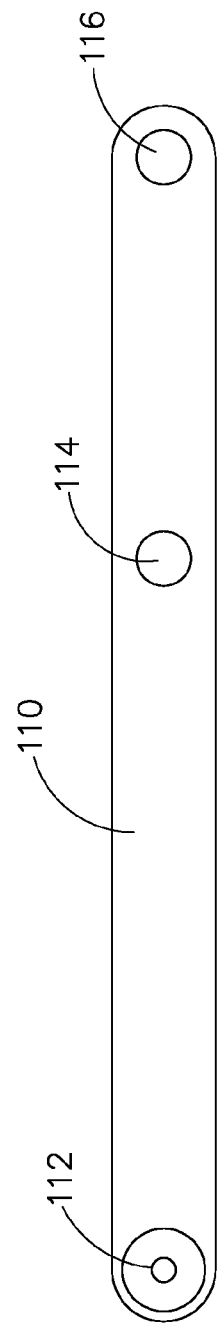
FIG. 11 depicts a top plan view of the drive arm of FIG. 10.
Figure 32:
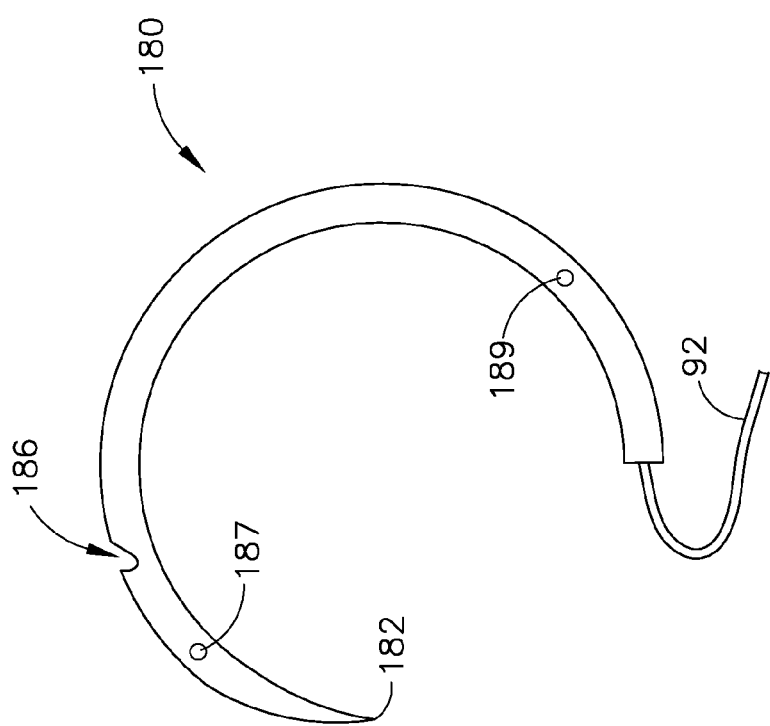
FIG. 32 depicts a bottom view of an exemplary needle suited for use with the end effector of FIG. 8.

FIG. 9 shows the gear assembly features of end effector (150) in greater detail. End effector (150) comprises a drive arm (110), gears (120, 130), and a rack (140) housed between frame base (160) and cover (152). Drive arm (110) comprises a drive pin (112) extending transversely from a distal end of drive arm (110), as shown in FIGS. 10-11. Drive pin (112) is similar to drive pin (72) of end effector (50) and is configured to engage needle return notch (87) and needle drive notch (89) of needle (80). As described above, notches (87, 89) have a transverse distal wall and allow drive pin (112) to engage notches (87, 89) to drive tip (82) of needle (80) forward. Notches (87, 89) also have an angled proximal exit to allow drive pin (112) to cammingly disengage notches (87, 89) in the reverse direction without applying a significant driving force on needle (80) in the reverse direction. Drive pin (112) may also engage needle (180) within end effector (150). As shown in FIG. 32, needle (180) is similar to needle (80), except that needle return notch (187) and needle drive notch (189) are positioned on a bottom surface of needle (180). Accordingly, drive pin (112) is configured to engage notches (187, 189) on a bottom surface of needle (180) to drive needle (180) forward. As shown in FIG. 11, drive arm (110) further comprises openings (114, 116) proximal to drive pin (112). Openings (114, 116) are longitudinally aligned. Opening (114) is configured to receive pin (128) of first gear (120) and opening (116) is configured to receive pin (138) of second gear (130).

Figure 12:
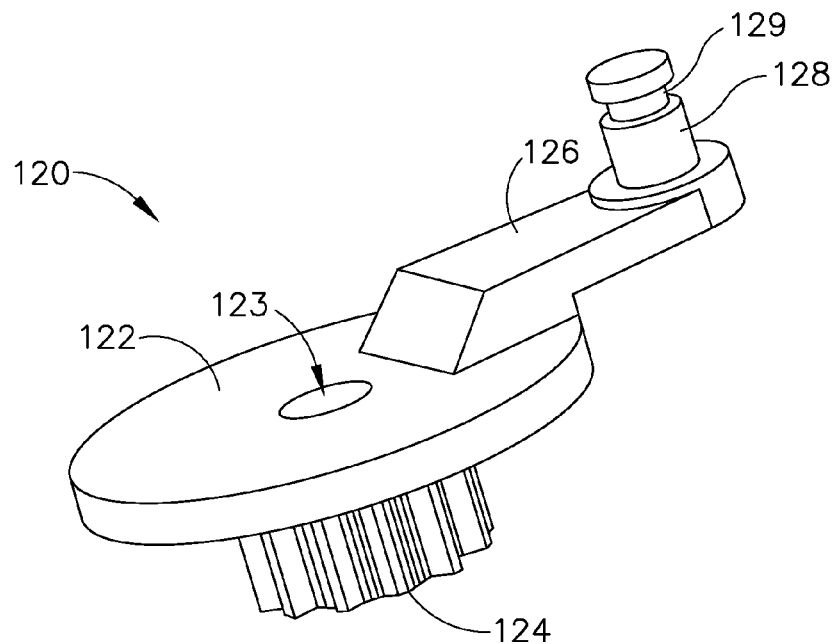
FIG. 12 depicts a perspective view of a gear of the end effector of FIG. 8.
Figure 13:
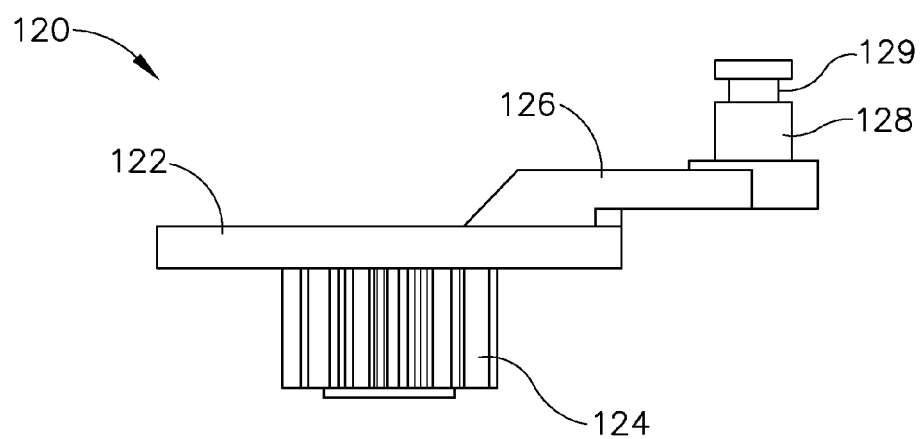
FIG. 13 depicts a side elevational view of the gear of FIG. 12.

First gear (120) comprises a plate (122), teeth (124), and an arm (126), as shown in FIGS. 12-13. Teeth (124) extend from plate (122) and are configured to engage rack (140). An opening (123) extends through plate (122) and teeth (124) such that first gear (120) is configured to receive a pin (163) of frame base (160) through opening (123). This maintains the longitudinal and lateral position of first gear (120) within frame base (160), while allowing first gear (120) to rotate relative to frame base (160). An arm (126) of first gear (120) extends outwardly from plate (122) and comprises a pin (128). Pin (128) is insertable within opening (114) of drive arm (110) such that pin (128) may rotate within opening (114). An annular recess (129) is provided on pin (128) to receive an e-clip (not shown) to maintain the position of drive arm (110) relative to pin (128). Second gear (130) is identical to first gear (120). Second gear (130) is positioned proximal to first gear (120) on pin (165) of frame base (160) to maintain the longitudinal and lateral position of second gear (130) within frame base (160), while allowing second gear (130) to rotate relative to frame base (160). Second gear (130) is spaced from first gear (120) such that the distance between the centerlines of gears (120, 130) is a whole multiple of the gear pitch. Pin (138) of second gear (130) is also insertable within opening (116) of drive arm (110) such that pin (138) may rotate within opening (116). Accordingly, first gear (120) and second gear (130) may be operated in unison to actuate drive arm (110) when first gear (120) and second gear (130) are rotated. Pins (128, 138) of gears (120, 130) therefore align to create a longitudinal axis that is parallel to the longitudinal axis of shaft (40). The distance from openings (123, 133) to each corresponding pin (128, 138) is equal to the centerline radius of needle (80). While two gears (120, 130) are used to maintain the longitudinal axis of drive arm (110) relative to end effector (150) in the present example, it should be understood that any other suitable number of gears (120, 130) may be used.

Figure 14:
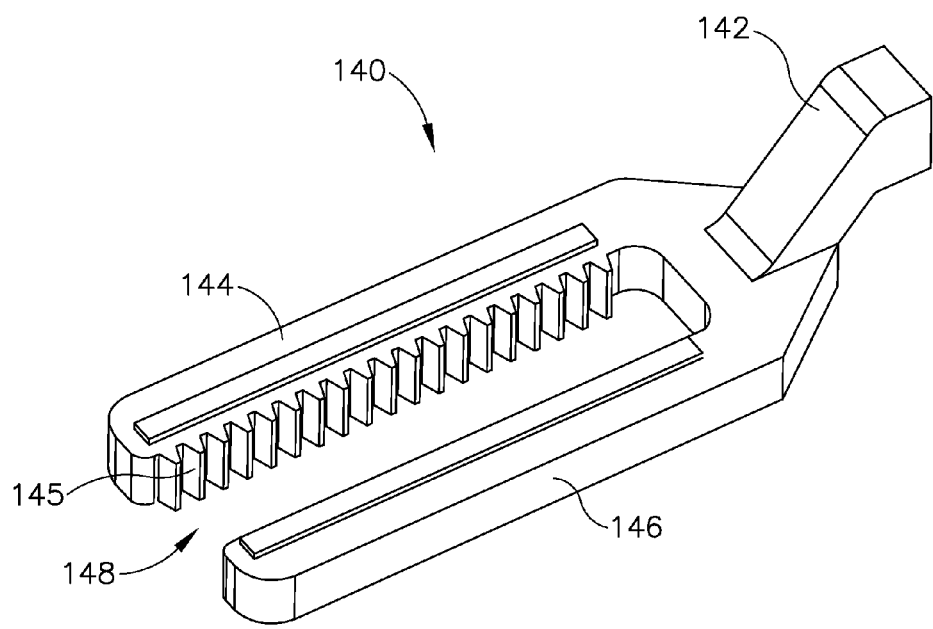
FIG. 14 depicts a perspective view of a rack of the end effector of FIG. 8.

Gears (120, 130) are configured to be actuated by rack (140). Rack (140) comprises arms (144, 146) defining a channel (148) extending between arms (144, 146), as shown in FIG. 14. A longitudinal row of teeth (145) is positioned on an interior of arm (144). Channel (148) is configured to receive gears (120, 130) such that teeth (124, 134) of gears (120, 130) engage the longitudinal row of teeth (145) of rack (140). A proximal portion (142) of rack (140) is coupled to a translation beam (149) (FIG. 9). Translation beam (149) may be coupled with trigger (24) such that trigger (24) may be pivoted relative to grip (22) to translate translation beam (149). Translation beam (149) may therefore translate rack (140) to rotate gears (120, 130). In the present example, rack (140) is translated distally to rotate gears (120, 130) in the counterclockwise direction and rack (140) is translated proximally to rotate gears (120, 130) in the clockwise direction. As gears (120, 130) rotate, drive arm (110) is actuated along an orbital path within end effector (150).

Figure 15:
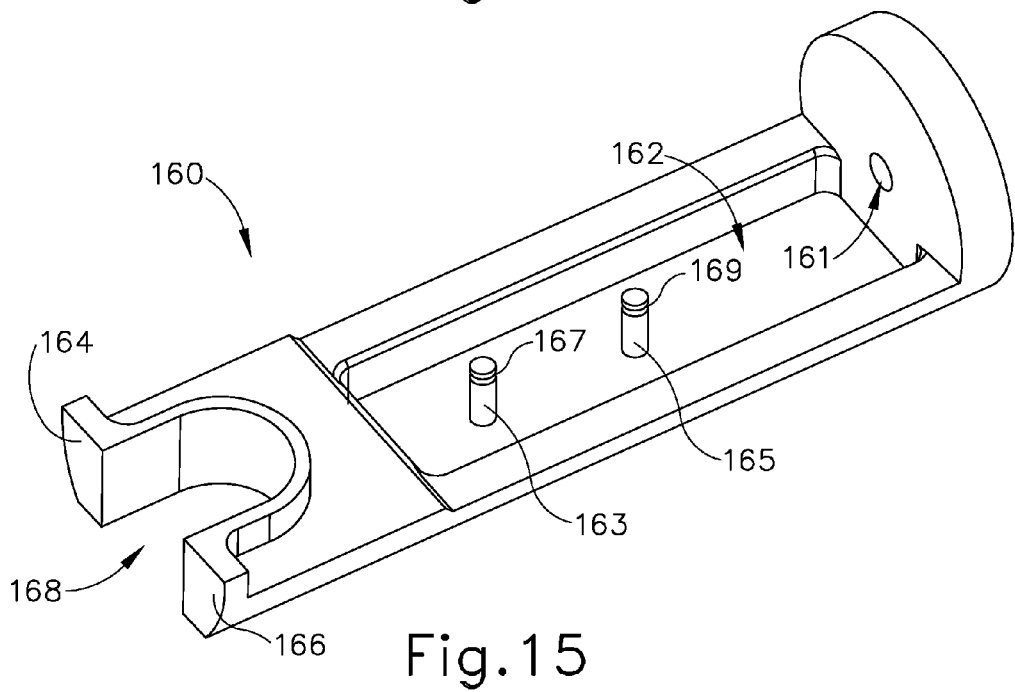
FIG. 15 depicts a perspective view of a base of the end effector of FIG. 8.

Rack (140) is translatable within frame base (160). Frame base (160) comprises a recess (162), pins (163, 165), and an opening (161), as shown in FIG. 15. Recess (162) is configured to receive rack (140) such that rack (140) is translatable within recess (162). Pins (163, 165) extend upwardly from within recess (162) and are configured to be positioned within channel (148) of rack (140). Pin (163) receives first gear (120) and pin (165) receives second gear (130). A proximal wall of frame base (160) defines an opening (161) configured to receive translation beam (149) such that translation beam (149) may translate within opening (161) and couple with rack (140). The distal portion of frame base (160) comprises arms (164, 166) that define a gap (168) for receiving tissue, to correspond to cover (152).

Cover (152) comprises a needle exit arm (154) and a needle entry arm (156), as shown in FIG. 16. Arms (154, 156) define a gap (158) for receiving tissue. A curved channel (155) is positioned within arms (154, 156) to receive needle (80) such that needle (80) is movable within channel (155). Channel (155) allows needle (80) to be visible within cover (152). Cover (152) is coupled with frame base (160) to house drive arm (110), gears (120, 130), and rack (140) within cover (152) and frame base (160). Accordingly, drive pin (112) of drive arm (110) is configured to extend within channel (155) of cover (152) to engage notches (87, 89) of needle (80). Drive arm (110) may then be actuated through gears (120, 130) and rack (140) to drive needle (80) with suture (92) through the tissue received in gaps (158, 168).

A. Exemplary Stages of Use

Figure 17A:
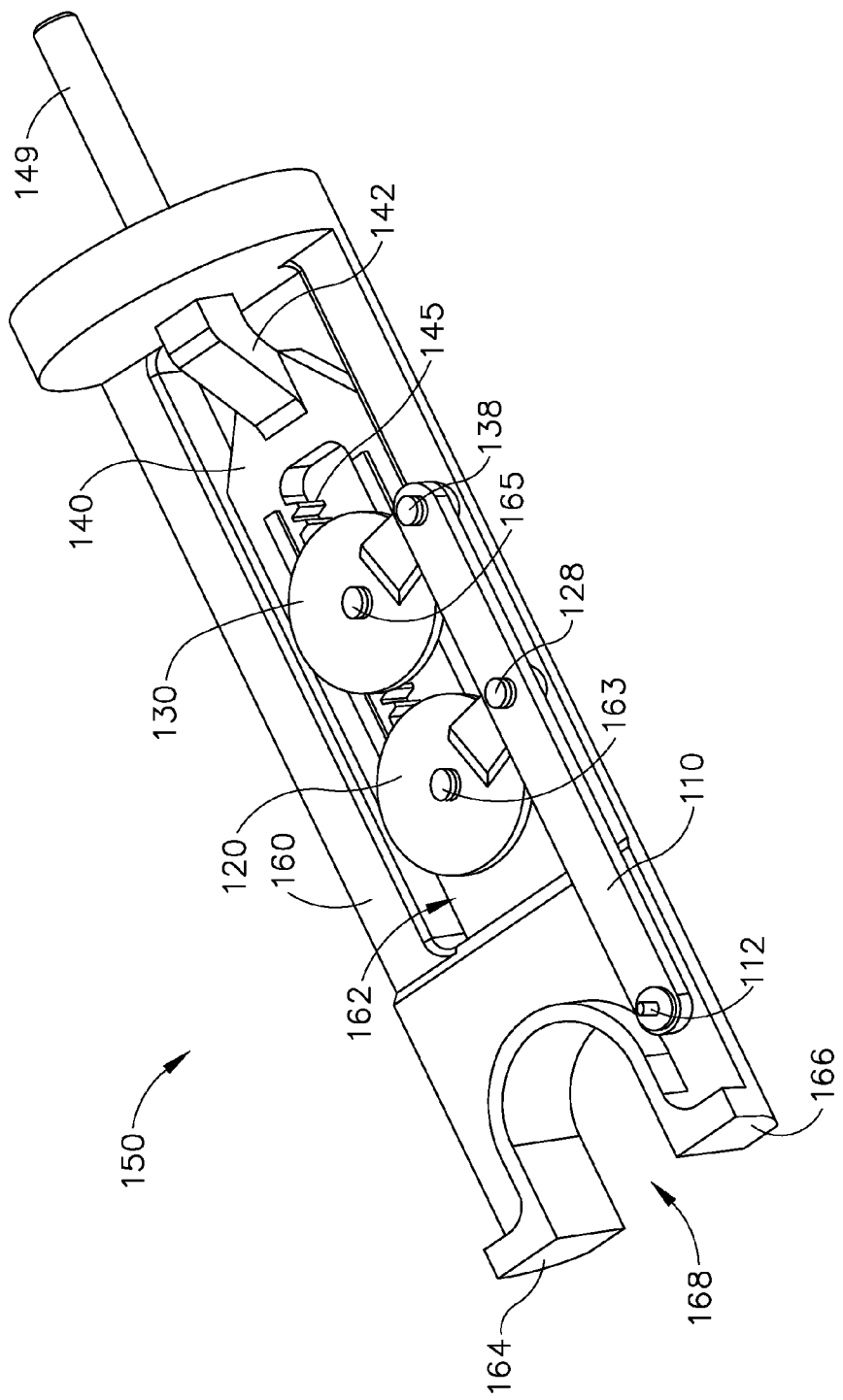
FIG. 17A depicts a perspective view of the end effector of FIG. 8 in a first position, with the cover removed.
Figure 17B:
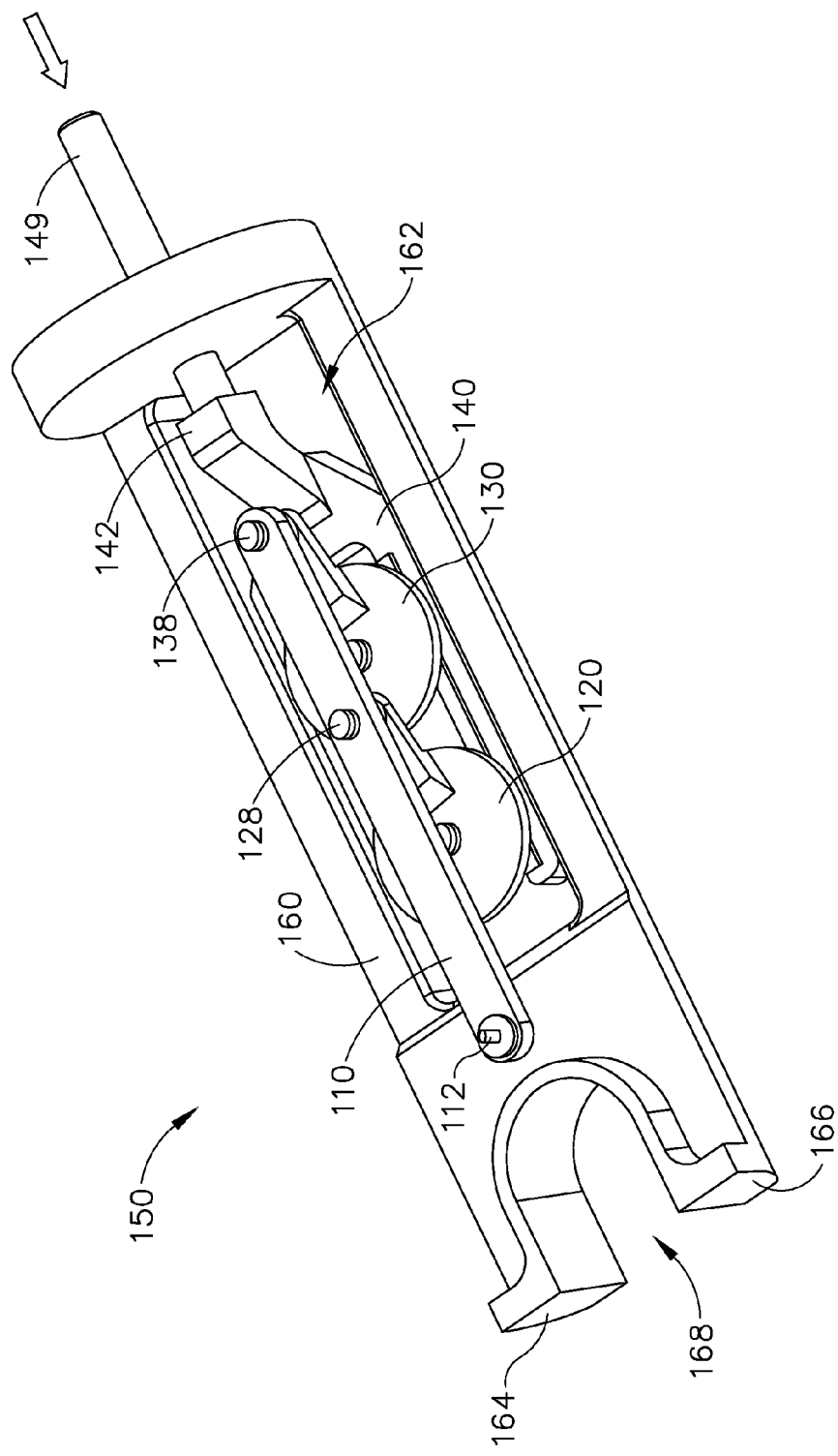
FIG. 17B depicts a perspective view of the end effector of FIG. 8 in a second position, with the cover removed.
Figure 17C:
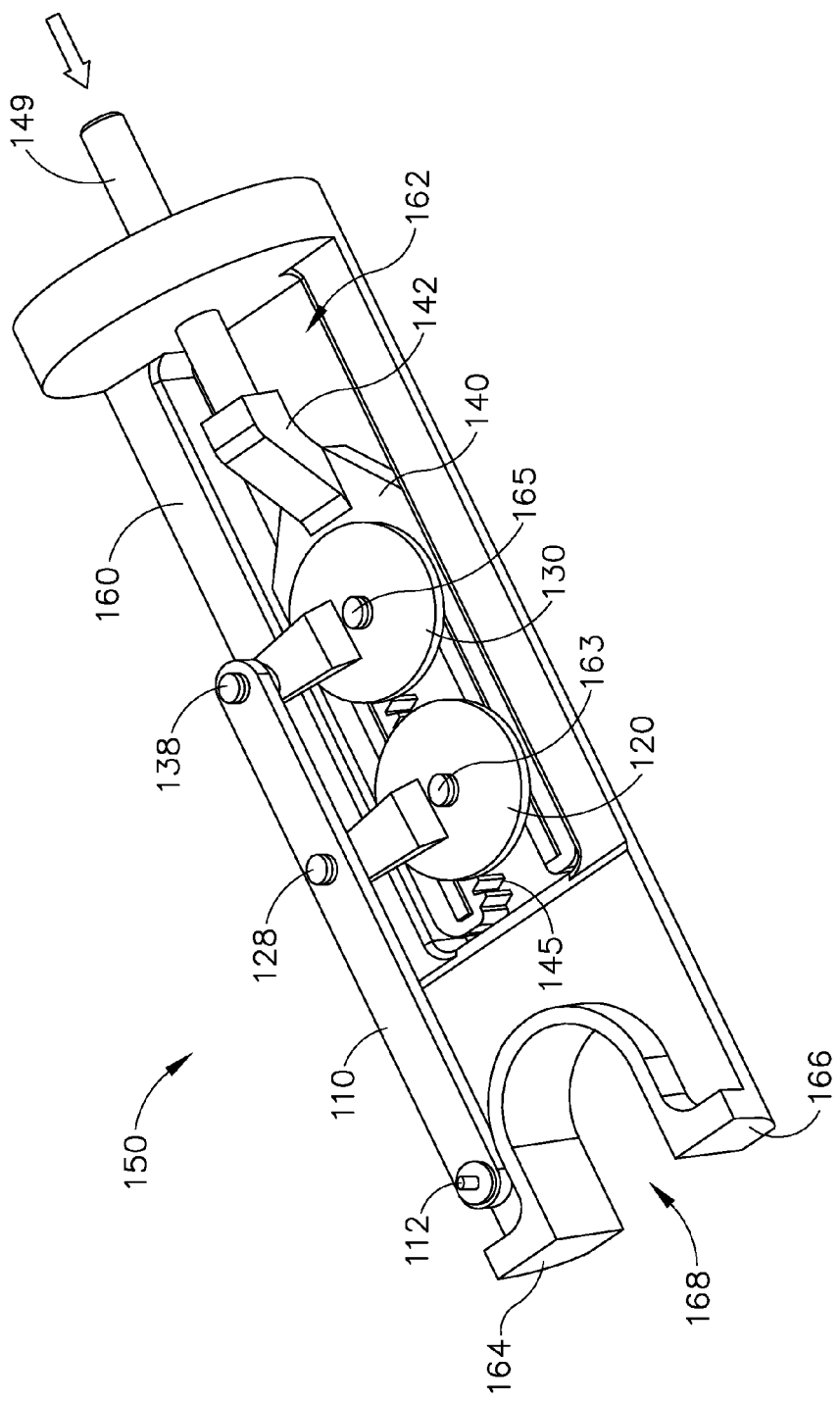
FIG. 17C depicts a perspective view of the end effector of FIG. 8 in a third position, with the cover removed.

End effector (150) may be actuated to securely close an incision (6) that splits two layers (2, 4) of tissue. Layers (2, 4) are positioned within gaps (158, 168) between arms (154, 156) and arms (164, 166). By way of example only, layers (2, 4) may be manipulated using a set of conventional tissue graspers and/or any other suitable instrumentation to position layers (2, 4) in gaps (158, 168). Needle (80) is positioned within channel (155) of cover (152) such that tip (82) of needle (80) is positioned within needle exit arm (154), similar to needle (80) in FIG. 6A. Drive arm (110) is positioned distally on a side portion of frame base (160), as shown in FIG. 17A, such that drive pin (112) engages needle drive notch (89). With layers (2, 4) suitably positioned, drive arm (110) is actuated as shown in FIGS. 17B-17C to drive needle (80) along a circular path (e.g. counterclockwise). For instance, trigger (24) may be pivoted toward grip (22) to translate translation beam (149) distally. Translation beam (149) thereby translates rack (140) distally within recess (162) of frame base (160). As rack (140) translates distally, teeth (145) of rack (140) engage teeth (124, 134) of gears (120, 130) to simultaneously rotate gears (120, 130) in the counterclockwise direction. As gears (120, 130) rotate, pins (128, 138) of gears (120, 130) actuate drive arm (110). Drive arm (110) thus moves proximally and centrally within frame base (160), as shown in FIG. 17B. As gears (120, 130) continue to rotate, drive arm (110) moves distally and to the opposing side portion of frame base (160), as shown in FIG. 17C. The orbital motion of drive arm (110) is transferred to needle (80) via drive pin (112) in needle drive notch (89). This orbital motion drives needle (80) approximately 180° along a circular path through channel (155) of cover (152), similar to needle (80) in FIG. 6B. During this travel, tip (82) pierces both layers (2, 4) of tissue, such that needle (80) is disposed in both layers (2, 4) of tissue.

Trigger (24) may then be released and pivoted away from grip (22) to translate translation beam (149) and rack (140) proximally. As rack (140) translates proximally, gears (120, 130) rotate clockwise to actuate drive arm (110). Accordingly, drive arm (110) moves proximally and centrally within frame base (160) to the position shown in FIG. 17B and continues to move distally and to the opposing side portion of frame base (160) to return to the position of FIG. 17A. When drive arm (110) is driven back to the position of FIG. 17A, drive pin (112) pivots away from needle (80) and out of engagement with needle drive notch (89), without actuating needle (80).

With arm (110) back in the initial position as shown in FIG. 17A after needle (80) has been driven 180 degrees into tissue, pin (112) is disposed in needle return notch (87), similar to needle (80) in FIG. 6C. This enables arm (110) to continue driving needle (80) along the circular path. Trigger (24) may again be squeezed toward grip (22) to translate translation beam (149) and rack (140) distally to thereby actuate gears (120, 130) and drive arm (110) to the position shown in FIG. 17C. This drives needle (80) through channel (155) of cover (152) completely through both layers (2, 4) of tissue. Needle (80) has thus traveled through a full 360° circular orbital path at this stage, and has thereby completed a full drive stroke, similar to needle (80) in FIG. 6D. This further results in needle (80) pulling suture (92) through both layers (2, 4) of tissue. Trigger (24) may then be released away from grip (22) to translate translation beam (149) and rack (140) proximally to thereby actuate gears (120, 130) and drive arm (110) back to the position shown in FIG. 17A. As drive arm (110) is actuated, arm (110) disengages needle return notch (87) in the same manner as the disengagement of pin (112) from needle drive notch (89) as described above, without actuating needle (80). Alternatively, needle (180) may be loaded within end effector (150) such that drive pin (112) engages notches (187, 189) on the bottom surface of needle (180) to drive needle (180) through layers (2, 4) of tissue.

With arm (110) being returned to the home position, the entire end effector (150) is then pulled away from layers (2, 4) of tissue to draw suture (92) through layers (2, 4) of tissue, similar to end effector (50) in FIG. 6E. After pulling additional length of suture (92) through layers (2, 4) of tissue, end effector (150) may be moved to another position along incision (6), with layers (2, 4) being repositioned in gaps (158, 168), such that the process may be repeated any number of times as desired to create a series of stitches along incision (6). The resulting stitches may appear similar to what is shown in FIG. 7. As shown, the portion of suture (92) disposed within layers (2, 4) of tissue is oriented generally transversely to the line defined by incision (60); while the portion of suture (92) that is external to layers (2, 4) of tissue is oriented obliquely relative to the line defined by incision (60). Of course, suture (92) may instead have any other types of configurations after being passed through layers (2, 4) of tissue to form a series of stitches. Other suitable ways in which instrument (10) may be used will be apparent to those of ordinary skill in the art in view of the teachings herein.

B. Exemplary Anti-Backup Features

Figure 18A:
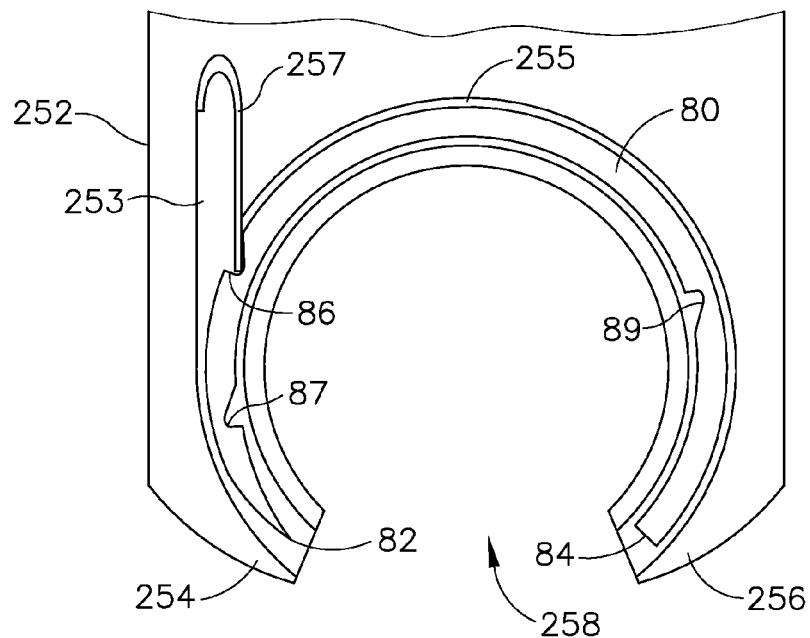
FIG. 18A depicts a top plan view of another exemplary cover for use with the end effector of FIG. 8, with a needle latched in a first position.
Figure 18B:
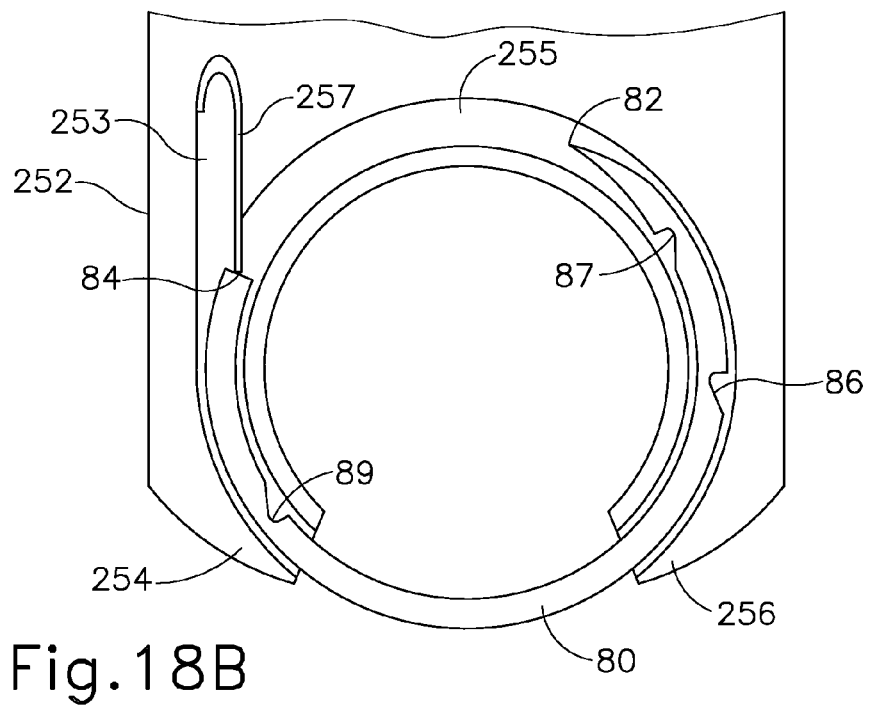
FIG. 18B depicts a top plan view of the cover of FIG. 18A, with the needle latched in a second position.

End effector (150) may include anti-backup features similar to pawl (64) of end effector (50). FIGS. 18A-18B show an alternative exemplary cover (252) that may be readily incorporated into end effector (150). Cover (252) is similar to cover (152), except that cover (252) comprises a channel (253) with a pawl (257) disposed within channel (253). Channel (253) is configured to maintain the longitudinal position of pawl (257). Pawl (257) extends within channel (255) of cover (252) to engage needle (80) to prevent needle (80) from travelling in the reverse direction within cover (252). Pawl (257) is similar to pawl (64) of end effector (50), except that pawl (257) is positioned within cover (252) instead of a frame base (60). Accordingly, pawl (257) is configured to engage anti-backup notch (86) of needle (80), as shown in FIG. 18A. This prevents needle (80) from travelling in the reverse direction when drive pin (112) disengages needle return notch (87). Pawl (257) is also configured to engage blunt end (84) of needle (80), as shown in FIG. 18B to prevent needle (80) from travelling in the reverse direction when drive pin (112) disengages needle drive notch (89).

Figure 19:
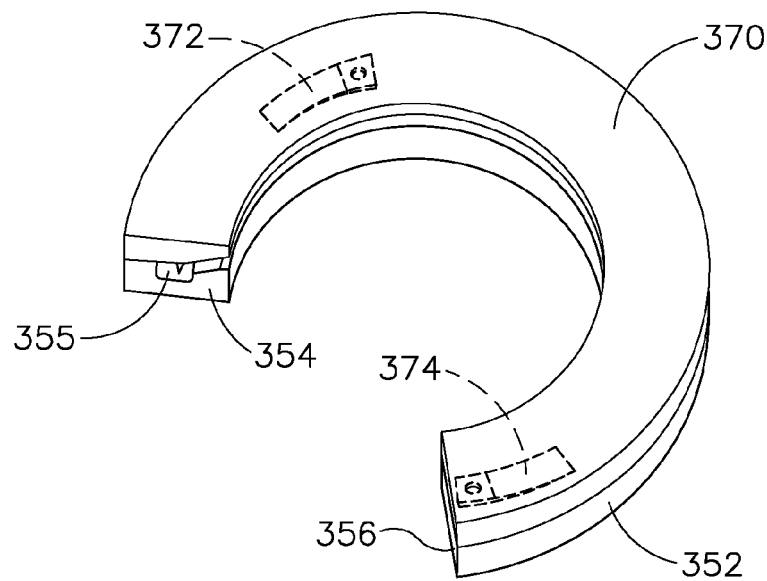
FIG. 19 depicts a partial perspective view of an exemplary latching member for use with the end effector of FIG. 8.
Figure 20:
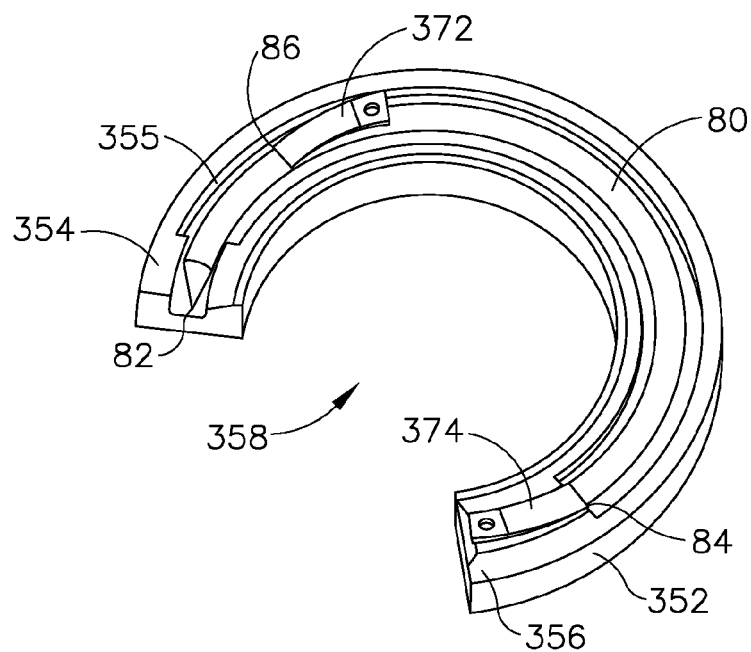
FIG. 20 depicts a partial perspective view of the latching member of FIG. 19, with a cover removed.

FIGS. 19-20 show another exemplary cover (352) with anti-backup features that may be readily incorporated into end effector (150). Cover (352) is similar to cover (152), except that cover (352) comprises a top portion (370). Top portion (370) comprises a pair of resilient pawl members (372, 374) extending downwardly from top portion (370). Top portion (370) is coupled to cover (352) such that resilient pawl members (372, 274) extend within channel (355) of cover (352), as shown in FIG. 20. Accordingly, resilient pawl members (372, 274) are configured to engage anti-backup notch (86) and/or blunt end (84) of needle (80) to prevent needle (80) from travelling in the reverse direction when drive pin (112) disengages needle return notch (87) and/or needle drive notch (89). Although two resilient pawl members (372, 374) are shown in the present example, any other suitable number of resilient pawl members (372, 374) may be used.

C. Exemplary Alternative Drive Arms

Figure 21:
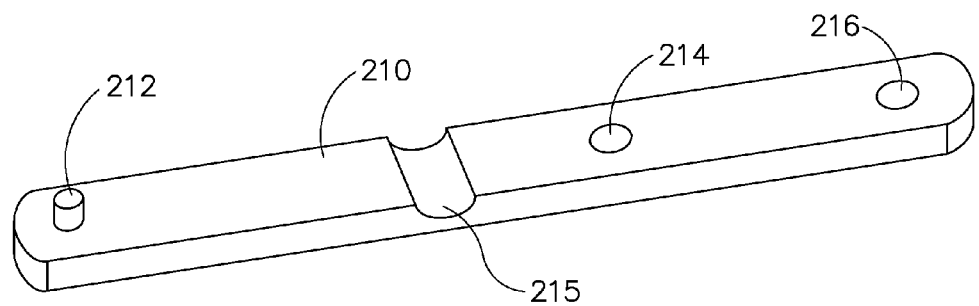
FIG. 21 depicts another exemplary drive arm for use with the end effector of FIG. 8.
Figure 22:
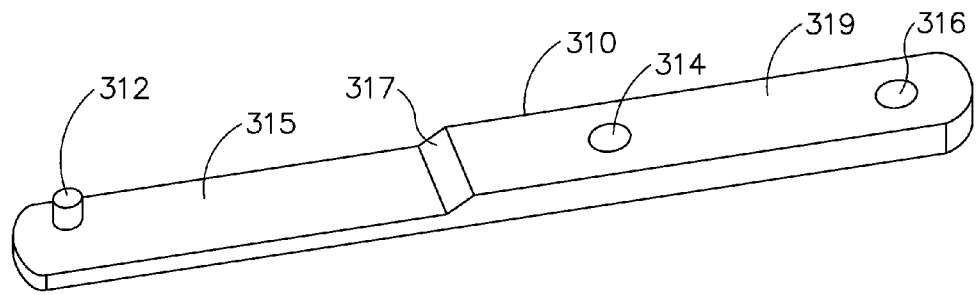
FIG. 22 depicts another exemplary drive arm for use with the end effector of FIG. 8.
Figure 23:
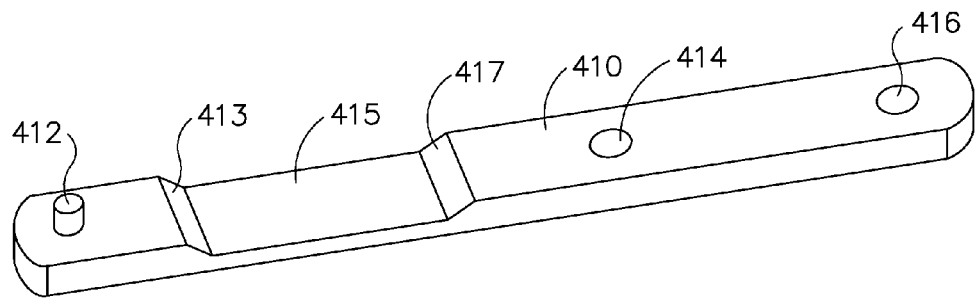
FIG. 23 depicts another exemplary drive arm for use with the end effector of FIG. 8.

In some instances, it may be desirable to tune the stiffness of drive arm (110) to adjust the amount of deflection allowed in drive arm (110) transverse to the longitudinal axis of drive arm (110), while maintaining the sufficient amount of stiffness in the lateral direction as well as in the proximal area of drive arm (110). For example, the deflectability of drive arm (110) may be tuned to facilitate disengagement of pin (112) from notch (189) on the bottom surface of needle (180), thereby facilitating travel of drive arm (110) to engage notch (187) while needle (180) is disposed in tissue. Similarly, the deflectability of drive arm (110) may be tuned to facilitate disengagement of pin (112) from notch (187) on the bottom surface of needle (180), thereby facilitating travel of drive arm (110) to re-engage notch (189) after needle (180) has been passed through tissue. Accordingly, drive arm (110) may be modified as shown in FIGS. 21-23. FIG. 21 shows an exemplary drive arm (210). Drive arm (210) is similar to drive arm (110), except that drive arm (210) comprises a recess (215) extending transversely across drive arm (210). Drive arm (310), shown in FIG. 22, is similar to drive arm (110), except that drive arm (310) comprises a distal portion (315) with a smaller thickness than proximal portion (319). In the present example, a ramped portion (317) is positioned between distal portion (315) and proximal portion (319) to provide a smooth transition between distal portion (315) and proximal portion (319). Another exemplary drive arm (410) is shown in FIG. 23. Drive arm (410) is similar to drive arm (110), except that drive arm (410) comprises a channel (415) positioned between drive pin (412) and opening (414). Ramped surfaces (413, 417) are positioned on either end of channel (415). Accordingly, drive arms (110, 210, 310, 410) have modified thicknesses that may adjust the stiffness of each drive arm (110, 210, 310, 410). Of course, other suitable methods to adjust drive arms (110, 210, 310, 410) will be apparent to one with ordinary skill in the art in view of the teachings herein.

D. Exemplary Alternative Drive Gear Assembly

Figure 24:
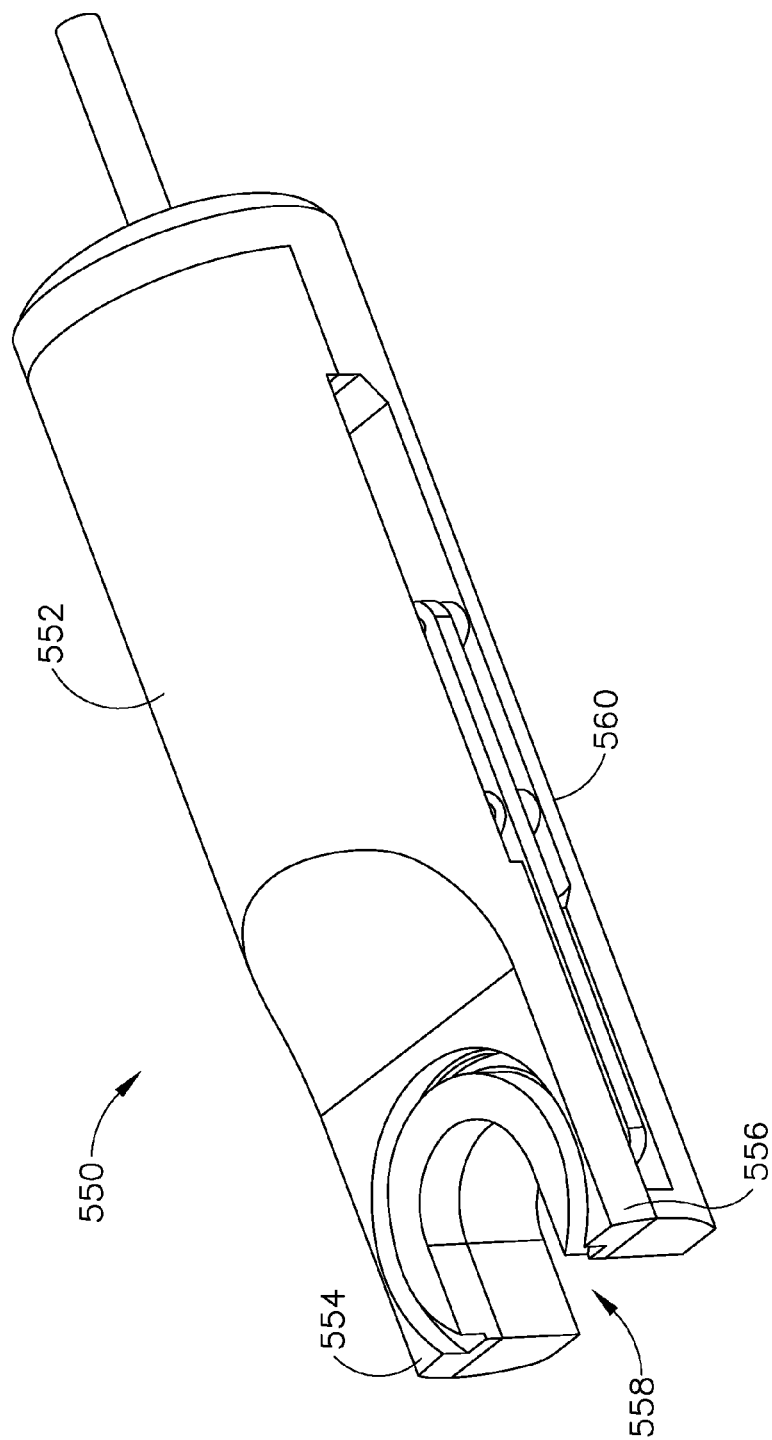
FIG. 24 depicts a perspective view of another exemplary end effector for use with the instrument of FIG. 1.
Figure 25:
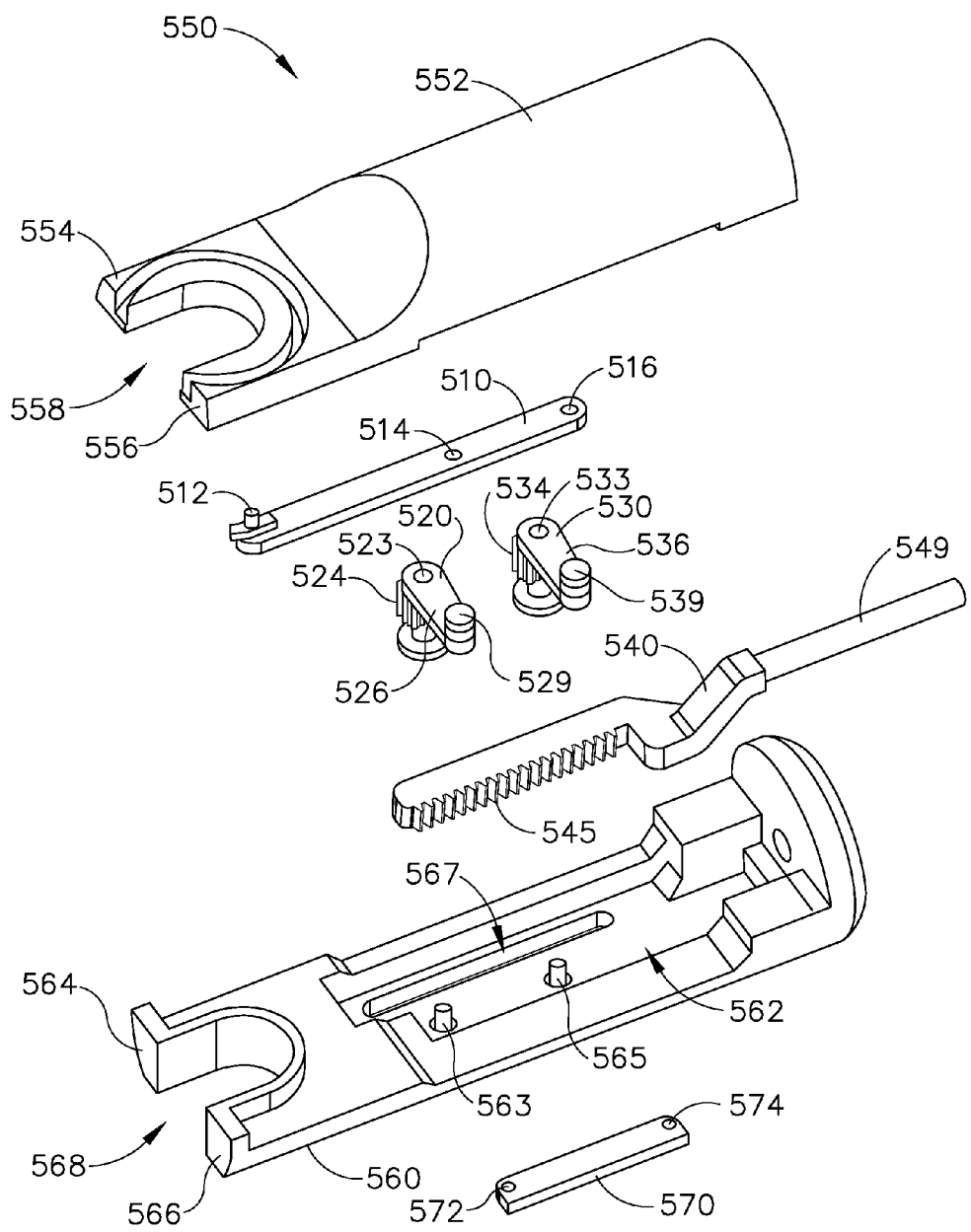
FIG. 25 depicts an exploded view of the end effector of FIG. 24.
Figure 26:
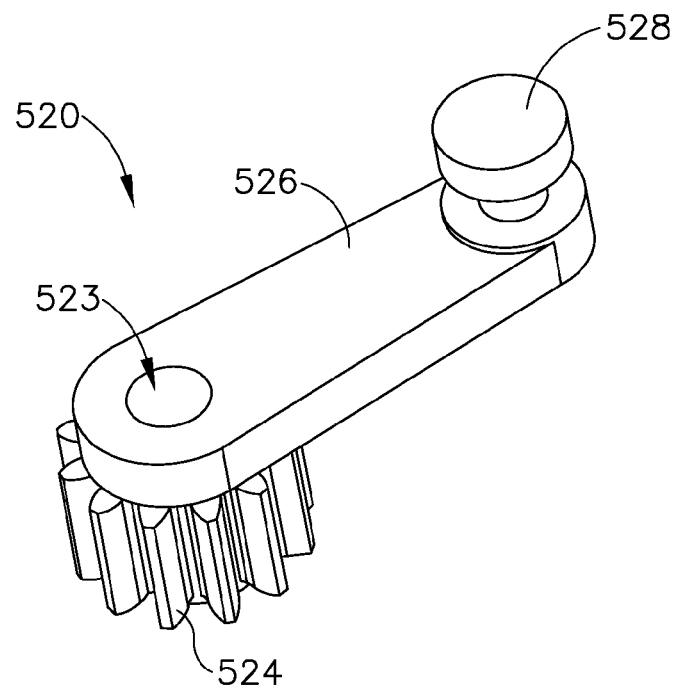
FIG. 26 depicts a perspective view of a gear of the end effector of FIG. 24.
Figure 27:
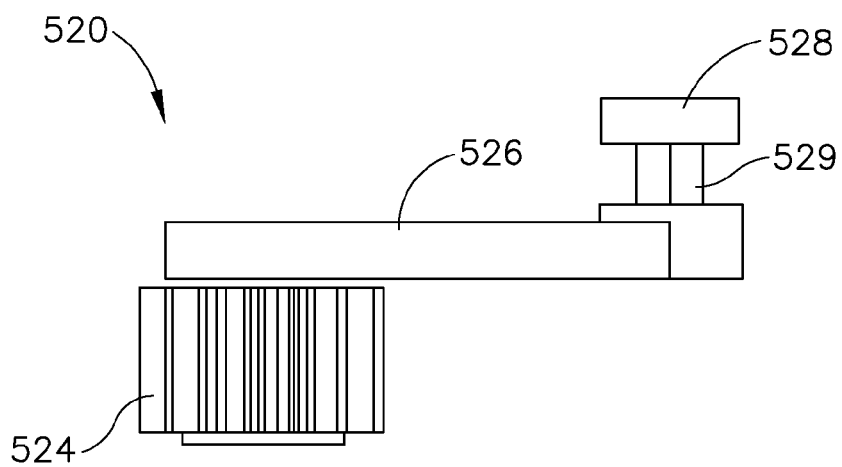
FIG. 27 depicts a side elevational view of the gear of FIG. 26.

FIGS. 24-25 show another exemplary end effector (550) with drive gear assembly features that may be readily incorporated into instrument (10). End effector (550) is similar to end effector (150) in that end effector (550) comprises a cover (552), drive arm (510), gears (520, 530), rack (540), and frame base (560). Cover (552) is substantially identical to cover (152) and drive arm (510) is substantially identical to drive arm (110). Gears (520, 530) are similar to gears (120, 130), except that arms (526, 536) of gears (520, 530) are coupled with teeth (524, 534) without a plate (122, 132). As shown in FIGS. 26-27, teeth (524) of first gear (520) extend from arm (526). An opening (523) extends through arm (526) and teeth (524) to receive a pin (563) of frame base (560). This maintains the longitudinal and lateral position of first gear (520) within frame base (560), while allowing first gear (520) to rotate relative to frame base (560). The opposing end of arm (526) comprises a pin (528) extending transversely from arm (526). Pin (528) is insertable within opening (514) of drive arm (510) such that pin (528) is rotatable within opening (514). An annular recess (529) is provided on pin (528) to receive an e-clip (not shown) to maintain the position of drive arm (510) relative to pin (528). Second gear (530) is substantially identical to first gear (520). Second gear (530) is positioned proximal to first gear (520) on pin (565) of frame base (560) to maintain the longitudinal and lateral position of second gear (530) within frame base (560), while allowing second gear (530) to rotate relative to frame base (560). Second gear (530) is spaced from first gear (520) such that the distance between the centerlines of gears (520, 530) is a whole multiple of the gear pitch. Pin (538) of second gear (530) is also insertable within opening (516) of drive arm (510) such that pin (538) may rotate within opening (516). Accordingly, first gear (520) and second gear (530) may be operated in unison to actuate drive arm (510) when first gear (520) and second gear (530) are rotated. While two gears (520, 530) are used to maintain the longitudinal axis of drive arm (510) relative to end effector (550) in the present example, it should be understood that any other suitable number of gears (520, 530) may be used.

Figure 28:
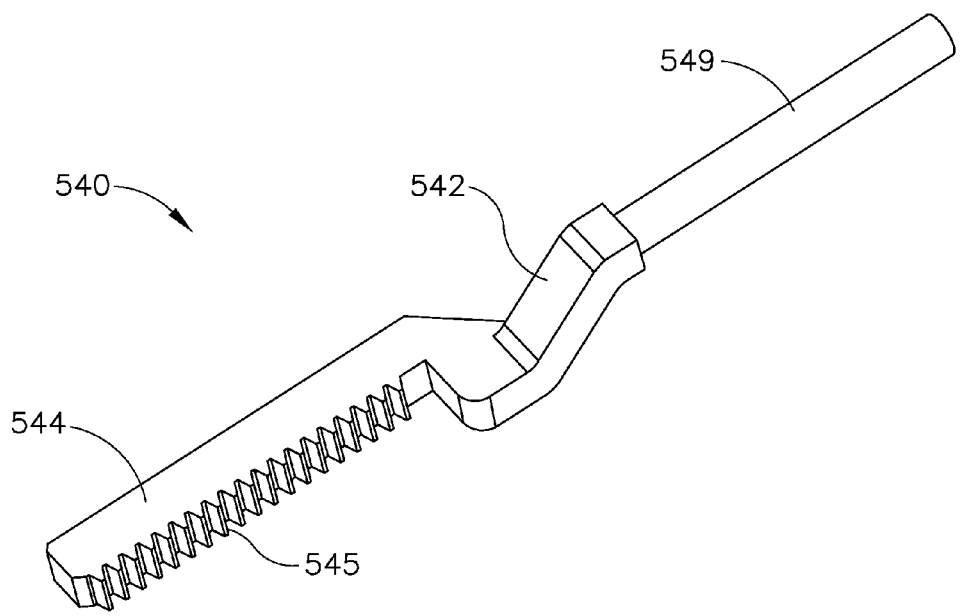
FIG. 28 depicts a perspective view of a rack of the end effector of FIG. 24.
Figure 29:
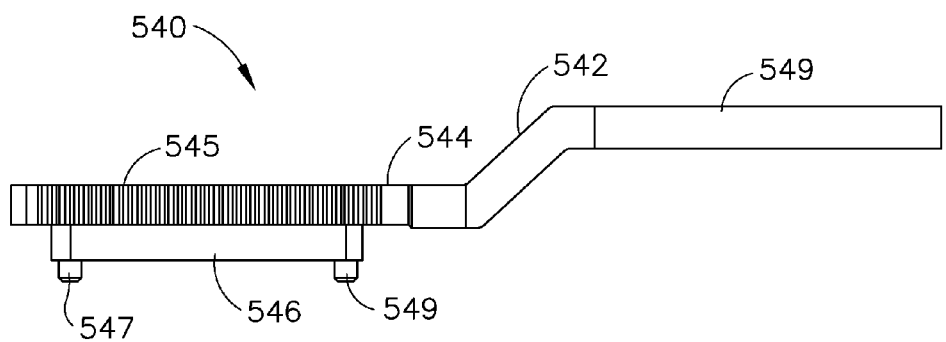
FIG. 29 depicts a side elevational view of the rack of FIG. 28.

Gears (520, 530) are configured to be actuated by rack (540). Rack (540) is similar to rack (140), except that rack (540) comprises a single arm (544), as shown in FIGS. 28-29. A longitudinal row of teeth (545) is positioned on the interior of arm (544) such that teeth (524, 534) of gears (520, 530) engage the longitudinal row of teeth (545) of rack (540). A proximal portion (542) of rack (540) is coupled to a translation beam (549). Translation beam (549) may be coupled with trigger (24) such that trigger (24) may be pivoted relative to grip (22) to translate translation beam (549). Translation beam (549) may therefore translate rack (540) to rotate gears (520, 530). In the present example, rack (540) is translated distally to rotate gears (520, 530) in the counterclockwise direction and rack (540) is translated proximally to rotate gears (520, 530) in the clockwise direction. As gears (520, 530) rotate, drive arm (510) is actuated within end effector (550). A protrusion (546) extends downwardly from arm (544) of rack (540), as shown in FIG. 29. A pin (547, 549) is positioned on each end of protrusion (546). Protrusion (546) may be received within frame base (560) to maintain the longitudinal alignment of rack (540) relative to end effector (550).

Figure 30:
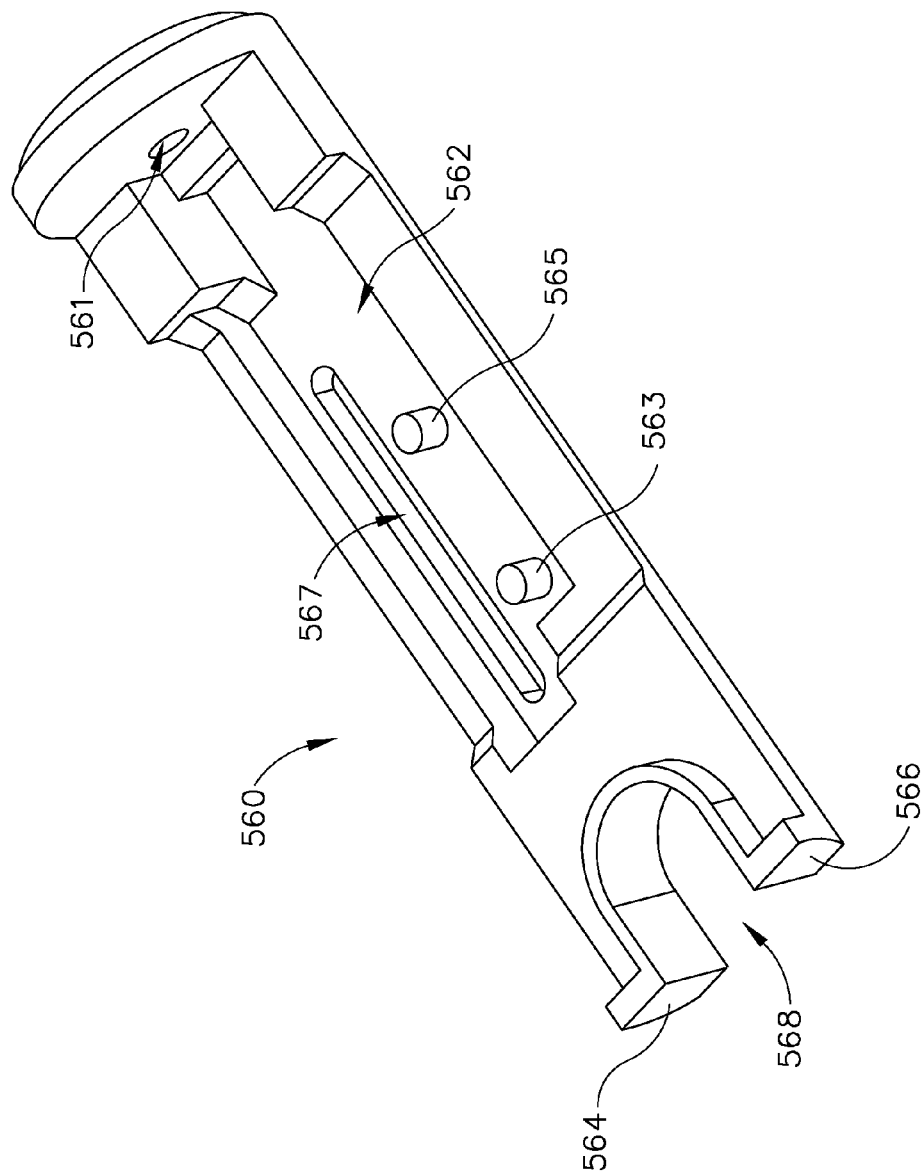
FIG. 30 depicts a perspective view of the a base of the end effector of FIG. 24.

Frame base (560) is similar to frame base (160), except that frame base (560) comprises a channel (567), as shown in FIG. 30. Channel (567) is configured to receive protrusion (546) of rack (540) such that protrusion (546) is translatable within channel (567). Pins (547, 549) of rack (540) extend beyond channel (567) to couple with bar (570) (FIG. 25). Bar (570) defines openings (572, 574) to receive pins (547, 549). Bar (570) is wider than channel (567) such that bar (570) maintains protrusion (546) of rack (540) within channel (567) of frame base (560).

Figure 31A:
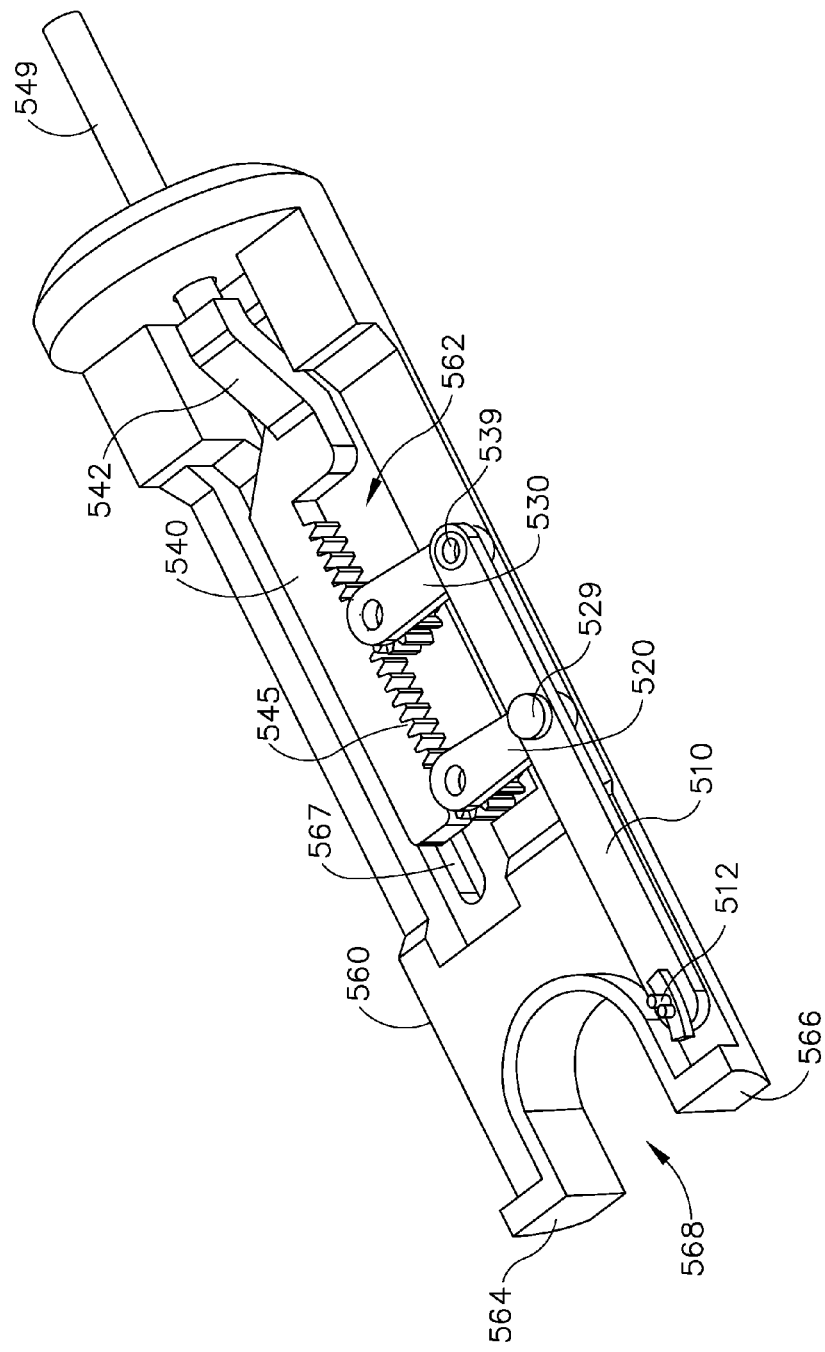
FIG. 31A depicts a perspective view of the end effector of FIG. 24 in a first position, with the cover removed.
Figure 31B:
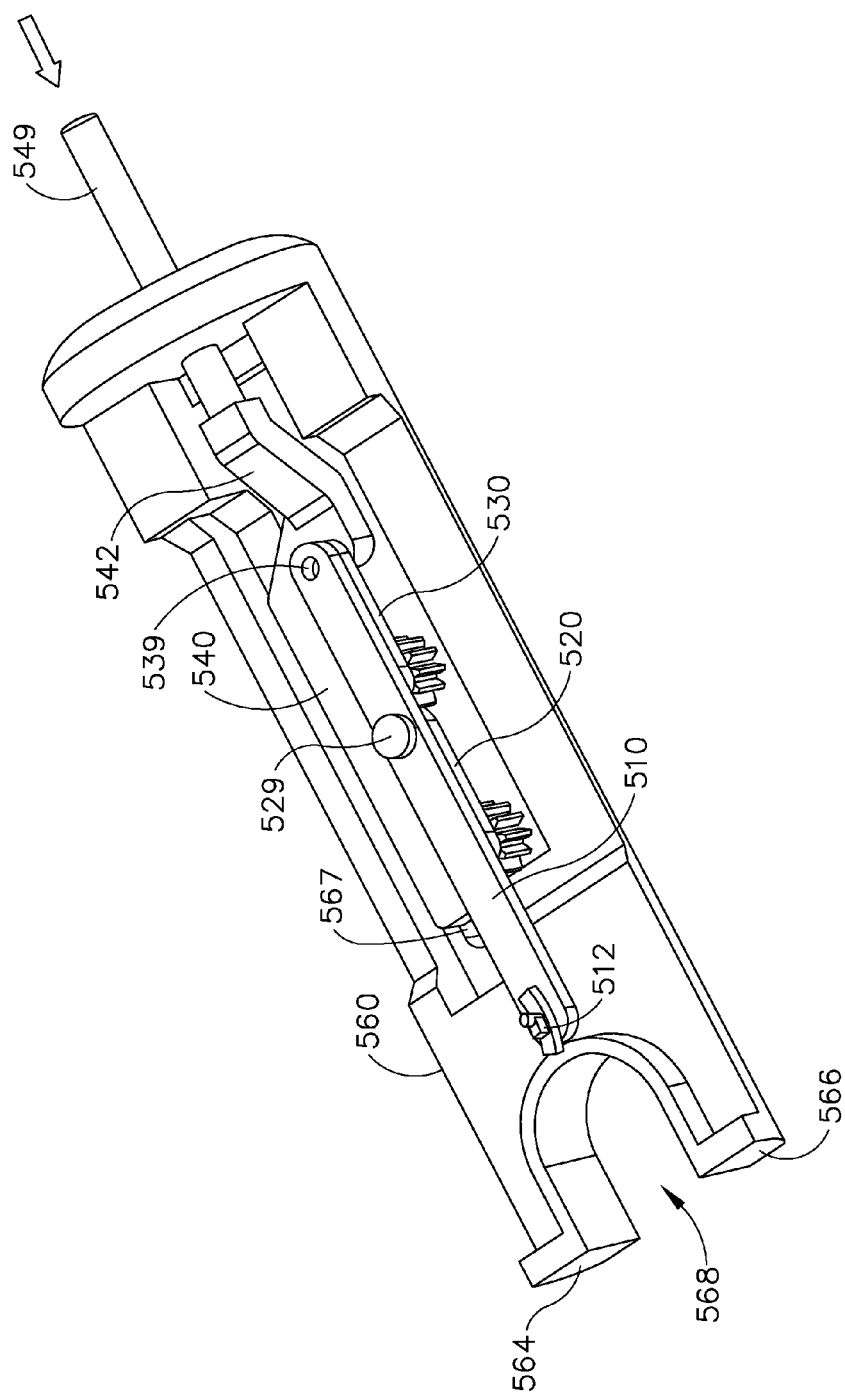
FIG. 31B depicts a perspective view of the end effector of FIG. 24 in a second position, with the cover removed.
Figure 31C:
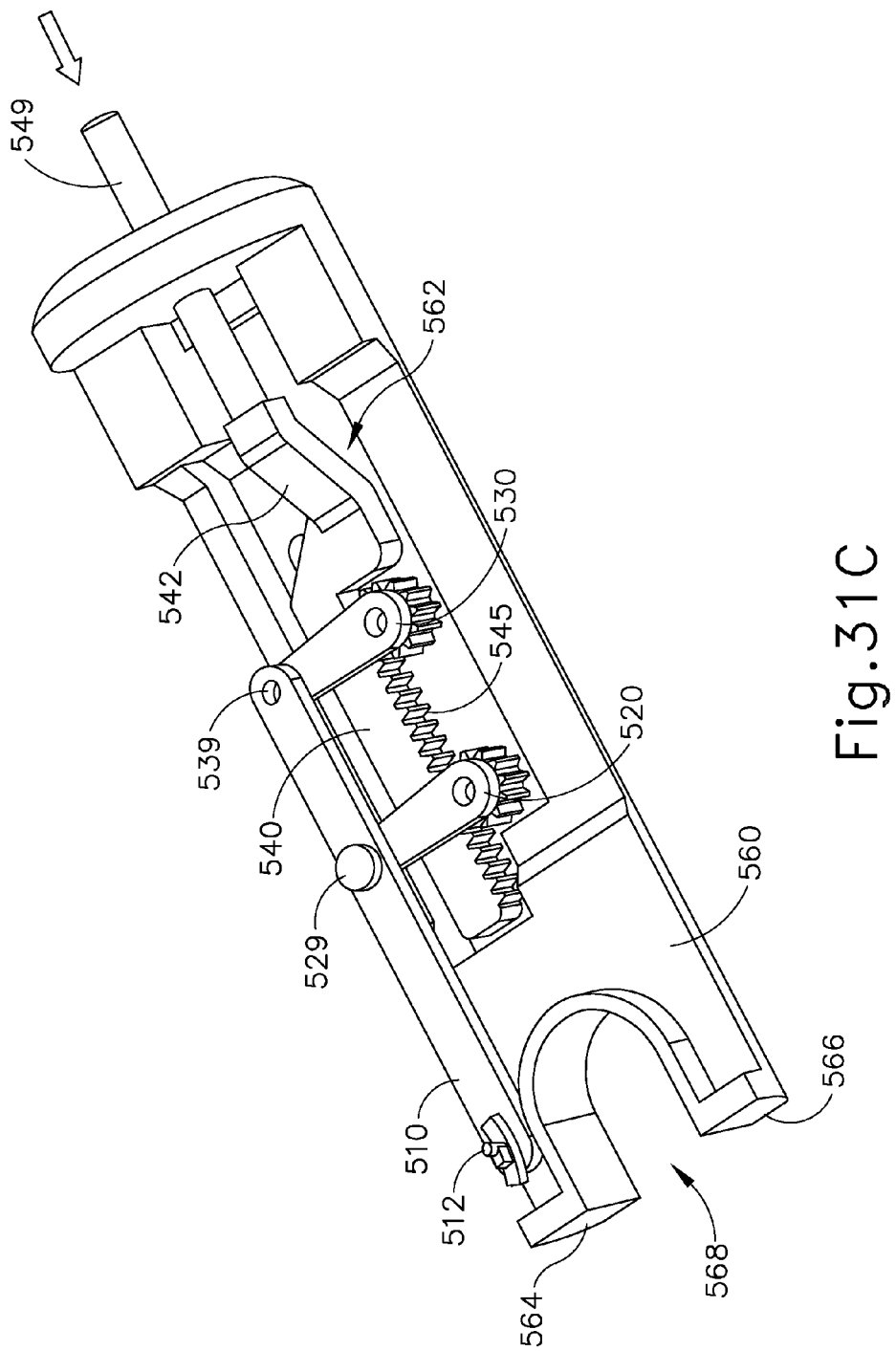
FIG. 31C depicts a perspective view of the end effector of FIG. 24 in a third position, with the cover removed.

Accordingly, end effector (550) may be actuated as shown in FIGS. 31A-31C. FIG. 31A shows drive arm (510) in an initial position such that drive arm (510) is positioned distally on a side portion of frame base (560). Translation beam (549) may then be translated distally by squeezing trigger (24) towards grip (22), as shown in FIG. 31B. As translation beam (549) translates distally, teeth (545) on rack (540) engage gears (520, 530) to rotate gears (520, 530). The rotation of gears (520, 520) thereby translates drive arm (510) proximally and centrally within frame base (560). As rack (540) continues to translate distally, as shown in FIG. 31C, gears (520, 530) continue to rotate to further translate drive arm (510) distally to the opposing side portion of frame base (560). Trigger (24) may then be released from grip (22) to translate translation beam (549) proximally. As translation beam (549) translates proximally, gears (520, 530) rotate in the opposing direction to return drive arm (510) to the initial position in FIG. 31A.

End effector (550) may therefore be actuated to securely close an incision (6) that splits two layers (2, 4) of tissue. Layers (2, 4) are positioned within gaps (558, 568) between arms (554, 556) and arms (564, 566). By way of example only, layers (2, 4) may be manipulated using a set of conventional tissue graspers and/or any other suitable instrumentation to position layers (2, 4) in gaps (558, 568). Needle (80) is positioned within channel (555) of cover (552) such that tip (82) of needle (80) is positioned within needle exit arm (554), similar to needle (80) in FIG. 6A. Drive arm (510) is positioned in the initial position, as shown in FIG. 31A, such that drive pin (512) engages needle drive notch (89). With layers (2, 4) suitably positioned, drive arm (510) is actuated as shown in FIGS. 31B-31C to drive needle (80) along a circular path (e.g. counterclockwise). For instance, trigger (24) may be pivoted toward grip (22) to translate translation beam (549) distally. Translation beam (549) thereby translates rack (540) distally within recess (562) of frame base (560). As rack (540) translates distally, teeth (545) of rack (540) engage teeth (524, 534) of gears (520, 530) to simultaneously rotate gears (520, 530) in the counterclockwise direction. The orbital motion of drive arm (510) is transferred to needle (80) via drive pin (512) in needle drive notch (89). This orbital motion drives needle (80) approximately 180° along a circular path through channel (555) of cover (552), similar to needle (80) in FIG. 6B. During this travel, tip (82) pierces both layers (2, 4) of tissue, such that needle (80) is disposed in both layers (2, 4) of tissue.

Trigger (24) may then be released and pivoted away from grip (22) to translate translation beam (549) and rack (540) proximally. As rack (540) translates proximally, gears (520, 530) rotate clockwise to actuate drive arm (510). Accordingly, drive arm (510) returns to the position of FIG. 31A. When drive arm (510) is returned to the position of FIG. 31A, drive pin (512) pivots away from needle (80) and out of engagement with needle drive notch (89), without actuating needle (80).

With arm (510) back in the initial position after needle (80) has been driven 180 degrees into tissue, pin (512) is disposed in needle return notch (87), similar to needle (80) in FIG. 6C. This enables arm (510) to continue driving needle (80) along the circular path. Trigger (24) may again be squeezed toward grip (22) to translate translation beam (549) and rack (540) distally to thereby actuate gears (520, 530) and drive arm (510) to the position shown in FIG. 31C. This drives needle (80) through channel (555) of cover (552) completely through both layers (2, 4) of tissue. Needle (80) has thus traveled through a full 360° circular orbital path at this stage, and has thereby completed a full drive stroke, similar to needle (80) in FIG. 6D. This further results in needle (80) pulling suture (92) through both layers (2, 4) of tissue. Trigger (24) may then be released away from grip (22) to translate translation beam (549) and rack (540) proximally to thereby actuate gears (520, 530) and drive arm (510) back to the position shown in FIG. 31A. As drive arm (510) is actuated, arm (510) disengages needle return notch (87) in the same manner as the disengagement of pin (512) from needle drive notch (89) as described above, without actuating needle (80). Alternatively, needle (180) may be loaded within end effector (550) such that drive pin (512) engages notches (187, 189) on the bottom surface of needle (180) to drive needle (180) through layers (2, 4) of tissue.

With arm (110) being returned to the home position, the entire end effector (550) is then pulled away from layers (2, 4) of tissue to draw suture (92) through layers (2, 4) of tissue, similar to end effector (50) in FIG. 6E. After pulling additional length of suture (92) through layers (2, 4) of tissue, end effector (550) may be moved to another position along incision (6), with layers (2, 4) being repositioned in gaps (558, 568), such that the process may be repeated any number of times as desired to create a series of stitches along incision (6). The resulting stitches may appear similar to what is shown in FIG. 7. As shown, the portion of suture (92) disposed within layers (2, 4) of tissue is oriented generally transversely to the line defined by incision (60); while the portion of suture (92) that is external to layers (2, 4) of tissue is oriented obliquely relative to the line defined by incision (60). Of course, suture (92) may instead have any other types of configurations after being passed through layers (2, 4) of tissue to form a series of stitches. Other suitable ways in which instrument (10) may be used will be apparent to those of ordinary skill in the art in view of the teachings herein.

III. Miscellaneous

It should be understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

While terms such as "clockwise" and "counterclockwise" have been used to describe directions of rotational movement during exemplary uses of instruments, it should be understood that these specific rotational directions are being provided only in reference to the examples depicted in the drawings. It is contemplated that rotational movement may be provided in directions opposite to those used above. Therefore, use of the terms "clockwise" and "counterclockwise" in any examples described herein should not be viewed as limiting in any way.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. In addition or in the alternative, various teachings herein may be readily combined with various teachings in U.S. Pat. No. 5,792,135, entitled "Articulated Surgical Instrument For Performing Minimally Invasive Surgery With Enhanced Dexterity and Sensitivity," issued Aug. 11, 1998, the disclosure of which is incorporated by reference herein; U.S. Pat. No. 5,817,084, entitled "Remote Center Positioning Device with Flexible Drive," issued Oct. 6, 1998, the disclosure of which is incorporated by reference herein; U.S. Pat. No. 5,878,193, entitled "Automated Endoscope System for Optimal Positioning," issued Mar. 2, 1999, the disclosure of which is incorporated by reference herein; U.S. Pat. No. 6,231,565, entitled "Robotic Arm DLUS for Performing Surgical Tasks," issued May 15, 2001, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 6,364,888, entitled "Alignment of Master and Slave in a Minimally Invasive Surgical Apparatus," issued Apr. 2, 2002, the disclosure of which is incorporated by reference herein; U.S. Pat. No. 7,524,320, entitled "Mechanical Actuator Interface System for Robotic Surgical Tools," issued Apr. 28, 2009, the disclosure of which is incorporated by reference herein; U.S. Pat. No. 7,691,098, entitled "Platform Link Wrist Mechanism," issued Apr. 6, 2010, the disclosure of which is incorporated by reference herein; U.S. Pat. No. 7,806,891, entitled "Repositioning and Reorientation of Master/Slave Relationship in Minimally Invasive Telesurgery," issued Oct. 5, 2010, the disclosure of which is incorporated by reference herein; and/or U.S. Pat. No. 7,824,401, entitled "Surgical Tool With Writed Monopolar Electrosurgical End Effectors," issued Nov. 2, 2010, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various versions in the present disclosure, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus for operating on tissue, the apparatus comprising:
   (a) a housing defining a channel, wherein the channel is configured to receive a needle such that the needle is movable within the channel;
   (b) a drive gear assembly positioned proximate to the needle, wherein the drive gear assembly comprises:
      (i) a first gear, and
      (ii) a rack, wherein the rack is translatable relative to the housing, wherein the rack comprises a first arm, wherein the first arm comprises a longitudinal row of teeth on an interior wall of the first arm, wherein the longitudinal row of teeth are configured to engage the first gear such that the rack is operable translate to thereby rotate the first gear; and
   (c) a drive arm coupled with the drive gear assembly, wherein the drive arm is configured to engage the needle to thereby cause orbital movement of the length of the needle along a circular path within the channel of the housing.

2. The apparatus of claim 1, wherein the housing comprises a base and a cover, wherein the base is coupled with the cover.

3. The apparatus of claim 2, wherein the channel is positioned within the cover.

4. The apparatus of claim 2, wherein the base defines a recess, wherein the rack is configured to translate within the recess of the base.

5. The apparatus of claim 1, wherein the drive gear assembly further comprises a second gear positioned proximal to the first gear, wherein the rack is further coupled with the second gear such that the rack is operable to rotate the second gear.

6. The apparatus of claim 5, wherein the housing comprises a first pin and a second pin, wherein the first pin is configured to receive the first gear, wherein the second pin is configured to receive the second gear.

7. The apparatus of claim 5, wherein the first gear comprises a first plate and a first arm, wherein the first arm extends from the first plate, wherein the second gear comprises a second plate and a second arm, wherein the second arm extends from the second plate.

8. The apparatus of claim 7, wherein the first arm comprises a first pin extending transversely from the first arm, wherein the second arm comprises a second pin extending transversely from the second arm, wherein the drive arm defines a first opening and a second opening, wherein the first opening is configured to receive the first pin, wherein the second opening is configured to receive the second pin.

9. The apparatus of claim 1, wherein the drive arm comprises a drive pin configured to extend through the channel of the housing, wherein the drive pin is configured to engage the needle.

10. The apparatus of claim 1, wherein the rack further comprises a second arm and a channel extending between the first and second arms, wherein the channel is configured to receive the first gear.

11. The apparatus of claim 1, wherein the rack comprises a protrusion, wherein the protrusion is configured to maintain the longitudinal alignment of the first arm relative to the housing.

12. The apparatus of claim 1, wherein the channel of the housing is arcuate, wherein the needle is configured to move orbitally through the channel.

13. The apparatus of claim 12, wherein the housing comprises a pawl, wherein the pawl is configured to engage the needle to prevent the needle from moving in a reverse direction.

14. The apparatus of claim 12, wherein the housing comprises a resilient member extending downwardly within the channel, wherein the resilient member is configured to engage the needle to prevent the needle from moving in a reverse direction.

15. The apparatus of claim 1, wherein the drive arm comprises a recess extending transversely across the drive arm.

16. The apparatus of claim 1 further comprising a handle portion, wherein the handle portion comprises an actuator configured to actuate the drive gear assembly.

17. The apparatus of claim 16, wherein the housing is rotatable relative to the handle portion.

18. The apparatus of claim 1, wherein the housing is configured to receive tissue, wherein the apparatus is configured to suture the tissue received within the housing.

19. An end effector comprising:
(a) a cover defining a channel, wherein the channel is configured to receive a needle such that the needle is movable within the channel; and
(b) a base couplable with the cover, wherein the base comprises:
 (i) a drive gear assembly, wherein the drive gear assembly comprises at least one gear,
 (ii) a rack, wherein the rack is translatable relative to the base, wherein the rack comprises a channel, wherein the at least one gear is positioned within the channel, wherein the channel comprises at least one row of teeth on an interior surface of the channel, wherein the at least one row of teeth is configured to engage the at least one gear such that the rack is operable translate to thereby rotate the at least one gear, and
 (iii) a drive arm coupled with of the at least one gear, wherein the drive gear assembly is operable to actuate the drive arm, wherein the drive arm is configured to engage the needle to thereby move the needle within the channel of the cover.

20. An end effector comprising:
(a) a housing defining a channel, wherein the channel is configured to receive a needle such that the needle is movable within the channel, wherein the channel is arcuate;
(b) a drive gear assembly positioned proximate to the needle, wherein the drive gear assembly comprises:
 (i) a rack, wherein the rack is translatable within the housing from a first position to a second position, wherein the rack comprises an arm, wherein an interior wall of the arm comprises a longitudinal row of teeth, and
 (ii) a gear, wherein the gear comprises a plurality of teeth configured to engage the longitudinal row of teeth of the rack, wherein the rack is operable to rotate the gear when the rack is translated from the first position to the second position; and
(c) a drive arm coupled with the gear of the drive gear assembly, wherein the drive arm is configured to engage a needle to thereby rotate the needle orbitally through the channel of the housing such that a sharp tip of the needle follows a circular path.

* * * * *